US006136547A

United States Patent [19]

[11] Patent Number: 6,136,547
[45] Date of Patent: Oct. 24, 2000

Tartaglia et al.

[54] NUCLEIC ACID MOLECULES ENCODING GLUTX AND USES THEREOF

[75] Inventors: Louis A. Tartaglia, Watertown; Xun Weng, Needham, both of Mass.

[73] Assignee: Millennium Pharmaceuticals, Inc., Cambridge, Mass.

[21] Appl. No.: 09/299,549

[22] Filed: Apr. 26, 1999

Related U.S. Application Data

[62] Division of application No. 09/031,392, Feb. 26, 1998, Pat. No. 5,942,398.

[51] Int. Cl.[7] .............................. G01N 33/53; C07K 5/00; C07K 14/00

[52] U.S. Cl. .............................. 435/7.1; 435/4; 435/7.4; 530/300; 530/350

[58] Field of Search .............................. 435/4, 7.1, 7.4; 530/300, 350

[56] References Cited

PUBLICATIONS

Fukumoto et al., "Cloning and Characterization of the Major Insulin–responsive Glucose Transporter . . . " J. of Biol. Chem. 264:7776–7779, 1989.

Kayano et al., "Human Facilitative Glucose Transporters" J. of Biol. Chem. 265:13276–13282, 1990.

Keller et al., "Functional Expression of the Human HepG2 and Rat Adipocyte Glucose . . . " J. of Biol. Chem. 264:18884–18889, 1989.

Mueckler et al., "Sequence and Structure of a Human Glucose Transporter" Science 229:941–945, 1985.

Thorens, B., "Glucose transporters in the regulation of intestinal, renal, and liver glucose fluxes" Amer. J. of Physiol. 270:G541–G553, 1996.

*Primary Examiner*—George C. Elliott
*Assistant Examiner*—Sean McGarry
*Attorney, Agent, or Firm*—Fish & Richardson P.C.

[57] ABSTRACT

The invention concerns the human gene encoding GLUTX, a glucose transporter. GLUTX nucleic acid and polypeptides, as well as molecules which increase or decrease expression or activity of GLUTX, are useful in the diagnosis and treatment of disorders associated with aberrant hexose transport.

14 Claims, 14 Drawing Sheets

TCG ACC CAC GCG TCC GGC CTT GGC AGA GTC TGG GGT CCC TGG ACT GAG CCA TCA GCT GGG
TCA CTG AGA CCC ATG GCA AGG AAA CAA AAT AGG AAT TCC AAG GAA CTG GGC CTA GTT CCC

CTC ACA GAT GAC ACC AGC CAC GCC GGG CCT CCA GGG CCA GGG AGG GCA CTG CTG GAG TGT

GAC CAC CTG AGG AGT GGG GTG CCA GGT GGA AGG AGA AGA AAG GAC TGG TCC TGC TCG CTC

CTC GTG GCC TCC CTC GCG GGC GCC TTC GGC TCC TCC TTC CTC TAC GGC TAC AAC CTG TCG

GTG GTG AAT GCC CCC ACC CCG TAC ATC AAG GCC TTT TAC AAT GAG TCA TGG GAA AGA AGG

CAT GGA CGT CCA ATA GAC CCA GAC ACT CTG ACT CTG CTC TGG TCT GTG ACT GTG TCC ATA

TTC GCC ATC GGT GGA CTT GTG GGG ACG TTA ATT GTG AAG ATG ATT GGA AAG GTT CTT GGG

FIG. 1A

AGG AAG CAC ACT TTG CTG GCC AAT AAT GGG TTT GCA ATT TCT GCT GCA TTG CTG ATG GCC

TGC TCG CTC CAG GCA GGA GCC TTT GAA ATG CTC ATT GTG GGA CGC TTC ATC ATG GGC ATA

GAT GGA GGC GTC GCC CTC AGT GTG CTC CCC ATG TAC CTC AGT GAG ATC TCA CCC AAG GAG

ATC CGT GGC TCT CTG GGG CAG GTG ACT GCC ATC TTT ATC TGC ATT GGC GTG TTC ACT GGG

CAG CTT CTG GGC CTG CCC GAG CTG CTG GGA AAG GAG AGT ACC TGG CCA TAC CTG TTT GGA

GTG ATT GTG GTC CCT GCC GTT GTC CAG CTG CTG AGC CTT CCC TTT CTC CCG GAC AGC CCA

CGC TAC CTG CTC TTG GAG AAG CAC AAC GAG GCA AGA GCT GTG AAA GCC TTC CAA ACG TTC

FIG. 1B

TTG GGT AAA GCA GAC GTT TCC CAA GAG GTA GAG GAG GTC CTG GCT GAG AGC CAC GTG CAG

AGG AGC ATC CGC CTG GTG TCC GTG CTG GAG CTG CTG AGA GCT CCC TAC GTC CGC TGG CAG

GTG GTC ACC GTG ATT GTC ACC ATG GCC TGC TAC CAG CTC TGT GGC CTC AAT GCA ATT TGG

TTC TAT ACC AAC AGC ATC TTT GGA AAA GCT GGG ATC CCT CCG GCA AAG ATC CCA TAC GTC

ACC TTG AGT ACA GGG GGC ATC GAG ACT TTG GCT GCC GTC TTC TCT GGT TTG GTC ATT GAG

CAC CTG GGA CGG AGA CCC CTC CTC ATT GGT GGC TTT GGG CTC ATG GGC CTC TTC TTT GGG

ACC CTC ACC ATC ACG CTG ACC CTG CAG GAC CAC GCC CCC TGG GTC CCC TAC CTG AGT ATC

GTG GGC ATT CTG GCC ATC ATC GCC TCT TTC TGC AGT GGG CCA GGT GGC ATC CCG TTC ATC

FIG. 1C

TTG ACT GGT GAG TTC TTC CAG CAA TCT CAG CGG CCG GCT GCC TTC ATC ATT GCA GGC ACC

GTC AAC TGG CTC TCC AAC TTT GCT GTT GGG CTC CTC TTC CCA TTC ATT CAG AAA AGT CTG

GAC ACC TAC TGT TTC CTA GTC TTT GCT ACA ATT TGT ATC ACA GGT GCT ATC TAC CTG TAT

TTT GTG CTG CCT GAG ACC AAA AAC AGA ACC TAT GCA GAA ATC AGC CAG GCA TTT TCC AAA

AGG AAC AAA GCA TAC CCA CCA GAA GAG AAA ATC GAC TCA GCT GTC ACT GAT GCT CCT GCT

TCT TCT CCT TTC ACT ACT CCG AAT ACA GCC TGG ATT CAA GCT GCC GCC ACC ACC ACC GCC

ACC AAA AAA GAA CAC CCA TTG TAA ACG GTC ATG TGG TAT TTC CTC AAC CTG GAA TGA CCT

FIG. 1D

TCC CCT ATC TTC TTC TCC TGG AGA ACA CCA AGT CAT GAT GTC AGA CAA GAG CTT GGA TTT
TGG AGA CAT GGG TTT GAA TTC CAG TCA TTC ATT CTT TTA TTC AGC AAA TAT TTA ACA AGT
ACT GAC ATG TCC CAT ATG TTG TTT TAC CCA CTG GTT ATA CAA TGG GAG GGA GAG AGA GAG
AGA GAG AGA GAG AGA GAT GCT ATT CTA AAA GCT TGA AGT CTA GGC TGT GCA CGG TGG CTC
ACG CCT GTA ATC CCA GCA CTT TGG GAG GCC GAG GTG GGT GGA TCG TGA GGT CAG GAG ATT
GAG ACC ATC CTG GCT AAC ATG GTG AAA CTC CCT CTC TAC TAA AAA TAC AAA AAA TTA GCT
GAG CAT GGT GGC GGG CGC CTG TAG TCC CAG CTA CTT GGG AGG CTG AGG CAG GAG AAT GGC
GTG AAC CCA GGA GGC GGA GCT TGC AGT GAG CCG AGA TCA CAC CAC CAC ACT CCA GCC TGG
GTG ACA GAG CCA GAC TCC GTC TCA AAA AAA AAA AAA AAA AAA AAA AAA AAA AAG GGC GGC
CGC

FIG. 1E met ala arg lys gln asn arg asn ser lys glu leu gly leu val pro leu thr asp asp thr ser his ala gly pro pro gly pro gly arg ala leu leu glu cys asp his leu arg ser gly val pro gly gly arg arg arg lys asp trp ser cys ser leu leu val ala ser leu ala gly ala phe gly ser ser phe leu tyr gly tyr asn leu ser val val asn ala pro thr pro tyr ile lys ala phe tyr asn glu ser trp glu arg arg his gly arg pro ile asp pro asp thr leu thr leu leu trp ser val thr val ser ile phe ala ile gly gly leu val gly thr leu ile val lys met ile gly lys val leu gly

FIG. 2A arg lys his thr leu leu ala asn asn gly phe ala ile ser ala ala leu leu met ala cys ser leu gln ala gly ala phe glu met leu ile val gly arg phe ile met gly ile asp gly gly val ala leu ser val leu pro met tyr leu ser glu ile ser pro lys glu ile arg gly ser leu gly gln val thr ala ile phe ile cys ile gly val phe thr gly gln leu leu gly leu pro glu leu leu gly lys glu ser thr trp pro tyr leu phe gly val ile val val pro ala val val gln leu leu ser leu pro phe leu pro asp ser pro arg tyr leu leu leu glu lys his asn glu ala arg ala val lys ala phe gln thr phe

FIG. 2B leu gly lys ala asp val ser gln glu val glu glu val leu ala glu ser his val gln arg ser ile arg leu val ser val leu glu leu leu arg ala pro tyr val arg trp gln val val thr val ile val thr met ala cys tyr gln leu cys gly leu asn ala ile trp phe tyr thr asn ser ile phe gly lys ala gly ile pro pro ala lys ile pro tyr val thr leu ser thr gly gly ile glu thr leu ala ala val phe ser gly leu val ile glu his leu gly arg arg pro leu leu ile gly gly phe gly leu met gly leu phe phe gly thr leu thr ile thr leu thr leu gln asp his ala pro trp val pro tyr leu ser ile val gly ile leu ala ile ile ala ser phe cys ser gly pro gly gly ile pro phe ile

FIG. 2C leu thr gly glu phe phe gln gln ser gln arg pro ala ala phe ile ile ala gly thr val asn trp leu ser asn phe ala val gly leu leu phe pro phe ile gln lys ser leu asp thr tyr cys phe leu val phe ala thr ile cys ile thr gly ala ile tyr leu tyr phe val leu pro glu thr lys asn arg thr tyr ala glu ile ser gln ala phe ser lys arg asn lys ala tyr pro pro glu glu lys ile asp ser ala val thr asp ala pro ala ser ser pro phe thr thr pro asn thr ala trp ile gln ala ala ala thr thr thr ala thr lys lys glu his pro leu

FIG. 2D

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
(A) LENGTH: 2343 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: Coding Sequence
(B) LOCATION: 73...1761

(xi) SEQUENCE DESCRIPTION: SEQ ID NO:1:

```
TCGACCCACG CGTCCGGCCT TGGCAGAGTC TGGGGTCCCT GGACTGAGCC ATCAGCTGGG     60

TCACTGAGAC CC ATG GCA AGG AAA CAA AAT AGG AAT TCC AAG GAA CTG GGC    111
              Met Ala Arg Lys Gln Asn Arg Asn Ser Lys Glu Leu Gly
               1               5                  10

CTA GTT CCC CTC ACA GAT GAC ACC AGC CAC GCC GGG CCT CCA GGG CCA      159
Leu Val Pro Leu Thr Asp Asp Thr Ser His Ala Gly Pro Pro Gly Pro
     15                  20                  25

GGG AGG GCA CTG CTG GAG TGT GAC CAC CTG AGG AGT GGG GTG CCA GGT      207
Gly Arg Ala Leu Leu Glu Cys Asp His Leu Arg Ser Gly Val Pro Gly
 30                  35                  40                  45

GGA AGG AGA AGA AAG GAC TGG TCC TGC TCG CTC CTC GTG GCC TCC CTC      255
Gly Arg Arg Arg Lys Asp Trp Ser Cys Ser Leu Leu Val Ala Ser Leu
                 50                  55                  60

GCG GGC GCC TTC GGC TCC TCC TTC CTC TAC GGC TAC AAC CTG TCG GTG      303
Ala Gly Ala Phe Gly Ser Ser Phe Leu Tyr Gly Tyr Asn Leu Ser Val
             65                  70                  75

GTG AAT GCC CCC ACC CCG TAC ATC AAG GCC TTT TAC AAT GAG TCA TGG      351
Val Asn Ala Pro Thr Pro Tyr Ile Lys Ala Phe Tyr Asn Glu Ser Trp
         80                  85                  90

GAA AGA AGG CAT GGA CGT CCA ATA GAC CCA GAC ACT CTG ACT CTG CTC      399
Glu Arg Arg His Gly Arg Pro Ile Asp Pro Asp Thr Leu Thr Leu Leu
     95                 100                 105

TGG TCT GTG ACT GTG TCC ATA TTC GCC ATC GGT GGA CTT GTG GGG ACG      447
Trp Ser Val Thr Val Ser Ile Phe Ala Ile Gly Gly Leu Val Gly Thr
110                 115                 120                 125
```

-continued

```
TTA ATT GTG AAG ATG ATT GGA AAG GTT CTT GGG AGG AAG CAC ACT TTG      495
Leu Ile Val Lys Met Ile Gly Lys Val Leu Gly Arg Lys His Thr Leu
                130                 135                 140

CTG GCC AAT AAT GGG TTT GCA ATT TCT GCT GCA TTG CTG ATG GCC TGC      543
Leu Ala Asn Asn Gly Phe Ala Ile Ser Ala Ala Leu Leu Met Ala Cys
            145                 150                 155

TCG CTC CAG GCA GGA GCC TTT GAA ATG CTC ATT GTG GGA CGC TTC ATC      591
Ser Leu Gln Ala Gly Ala Phe Glu Met Leu Ile Val Gly Arg Phe Ile
        160                 165                 170

ATG GGC ATA GAT GGA GGC GTC GCC CTC AGT GTG CTC CCC ATG TAC CTC      639
Met Gly Ile Asp Gly Gly Val Ala Leu Ser Val Leu Pro Met Tyr Leu
    175                 180                 185

AGT GAG ATC TCA CCC AAG GAG ATC CGT GGC TCT CTG GGG CAG GTG ACT      687
Ser Glu Ile Ser Pro Lys Glu Ile Arg Gly Ser Leu Gly Gln Val Thr
190                 195                 200                 205

GCC ATC TTT ATC TGC ATT GGC GTG TTC ACT GGG CAG CTT CTG GGC CTG      735
Ala Ile Phe Ile Cys Ile Gly Val Phe Thr Gly Gln Leu Leu Gly Leu
                210                 215                 220

CCC GAG CTG CTG GGA AAG GAG AGT ACC TGG CCA TAC CTG TTT GGA GTG      783
Pro Glu Leu Leu Gly Lys Glu Ser Thr Trp Pro Tyr Leu Phe Gly Val
            225                 230                 235

ATT GTG GTC CCT GCC GTT GTC CAG CTG CTG AGC CTT CCC TTT CTC CCG      831
Ile Val Val Pro Ala Val Val Gln Leu Leu Ser Leu Pro Phe Leu Pro
        240                 245                 250

GAC AGC CCA CGC TAC CTG CTC TTG GAG AAG CAC AAC GAG GCA AGA GCT      879
Asp Ser Pro Arg Tyr Leu Leu Leu Glu Lys His Asn Glu Ala Arg Ala
    255                 260                 265

GTG AAA GCC TTC CAA ACG TTC TTG GGT AAA GCA GAC GTT TCC CAA GAG      927
Val Lys Ala Phe Gln Thr Phe Leu Gly Lys Ala Asp Val Ser Gln Glu
270                 275                 280                 285

GTA GAG GAG GTC CTG GCT GAG AGC CAC GTG CAG AGG AGC ATC CGC CTG      975
Val Glu Glu Val Leu Ala Glu Ser His Val Gln Arg Ser Ile Arg Leu
                290                 295                 300

GTG TCC GTG CTG GAG CTG CTG AGA GCT CCC TAC GTC CGC TGG CAG GTG     1023
Val Ser Val Leu Glu Leu Leu Arg Ala Pro Tyr Val Arg Trp Gln Val
            305                 310                 315

GTC ACC GTG ATT GTC ACC ATG GCC TGC TAC CAG CTC TGT GGC CTC AAT     1071
Val Thr Val Ile Val Thr Met Ala Cys Tyr Gln Leu Cys Gly Leu Asn
        320                 325                 330

GCA ATT TGG TTC TAT ACC AAC AGC ATC TTT GGA AAA GCT GGG ATC CCT     1119
Ala Ile Trp Phe Tyr Thr Asn Ser Ile Phe Gly Lys Ala Gly Ile Pro
    335                 340                 345

CCG GCA AAG ATC CCA TAC GTC ACC TTG AGT ACA GGG GGC ATC GAG ACT     1167
Pro Ala Lys Ile Pro Tyr Val Thr Leu Ser Thr Gly Gly Ile Glu Thr
350                 355                 360                 365

TTG GCT GCC GTC TTC TCT GGT TTG GTC ATT GAG CAC CTG GGA CGG AGA     1215
Leu Ala Ala Val Phe Ser Gly Leu Val Ile Glu His Leu Gly Arg Arg
                370                 375                 380

CCC CTC CTC ATT GGT GGC TTT GGG CTC ATG GGC CTC TTC TTT GGG ACC     1263
Pro Leu Leu Ile Gly Gly Phe Gly Leu Met Gly Leu Phe Phe Gly Thr
            385                 390                 395

CTC ACC ATC ACG CTG ACC CTG CAG GAC CAC GCC CCC TGG GTC CCC TAC     1311
Leu Thr Ile Thr Leu Thr Leu Gln Asp His Ala Pro Trp Val Pro Tyr
        400                 405                 410

CTG AGT ATC GTG GGC ATT CTG GCC ATC ATC GCC TCT TTC TGC AGT GGG     1359
Leu Ser Ile Val Gly Ile Leu Ala Ile Ile Ala Ser Phe Cys Ser Gly
    415                 420                 425

CCA GGT GGC ATC CCG TTC ATC TTG ACT GGT GAG TTC TTC CAG CAA TCT     1407
Pro Gly Gly Ile Pro Phe Ile Leu Thr Gly Glu Phe Phe Gln Gln Ser
430                 435                 440                 445
```

-continued

```
CAG CGG CCG GCT GCC TTC ATC ATT GCA GGC ACC GTC AAC TGG CTC TCC     1455
Gln Arg Pro Ala Ala Phe Ile Ile Ala Gly Thr Val Asn Trp Leu Ser
                450                 455                 460

AAC TTT GCT GTT GGG CTC CTC TTC CCA TTC ATT CAG AAA AGT CTG GAC     1503
Asn Phe Ala Val Gly Leu Leu Phe Pro Phe Ile Gln Lys Ser Leu Asp
            465                 470                 475

ACC TAC TGT TTC CTA GTC TTT GCT ACA ATT TGT ATC ACA GGT GCT ATC     1551
Thr Tyr Cys Phe Leu Val Phe Ala Thr Ile Cys Ile Thr Gly Ala Ile
        480                 485                 490

TAC CTG TAT TTT GTG CTG CCT GAG ACC AAA AAC AGA ACC TAT GCA GAA     1599
Tyr Leu Tyr Phe Val Leu Pro Glu Thr Lys Asn Arg Thr Tyr Ala Glu
    495                 500                 505

ATC AGC CAG GCA TTT TCC AAA AGG AAC AAA GCA TAC CCA CCA GAA GAG     1647
Ile Ser Gln Ala Phe Ser Lys Arg Asn Lys Ala Tyr Pro Pro Glu Glu
510                 515                 520                 525

AAA ATC GAC TCA GCT GTC ACT GAT GCT CCT GCT TCT TCT CCT TTC ACT     1695
Lys Ile Asp Ser Ala Val Thr Asp Ala Pro Ala Ser Ser Pro Phe Thr
                530                 535                 540

ACT CCG AAT ACA GCC TGG ATT CAA GCT GCC GCC ACC ACC ACC GCC ACC     1743
Thr Pro Asn Thr Ala Trp Ile Gln Ala Ala Ala Thr Thr Thr Ala Thr
            545                 550                 555

AAA AAA GAA CAC CCA TTG TAAACGGTCA TGTGGTATTT CCTCAACCTG GAATGACC   1799
Lys Lys Glu His Pro Leu
        560

TTCCCCTATC TTCTTCTCCT GGAGAACACC AAGTCATGAT GTCAGACAAG AGCTTGGATT   1859

TTGGAGACAT GGGTTTGAAT TCCAGTCATT CATTCTTTTA TTCAGCAAAT ATTTAACAAG   1919

TACTGACATG TCCCATATGT TGTTTTACCC ACTGGTTATA CAATGGGAGG GAGAGAGAGA   1979

GAGAGAGAGA GAGAGAGATG CTATTCTAAA AGCTTGAAGT CTAGGCTGTG CACGGTGGCT   2039

CACGCCTGTA ATCCCAGCAC TTTGGGAGGC CGAGGTGGGT GGATCGTGAG GTCAGGAGAT   2099

TGAGACCATC CTGGCTAACA TGGTGAAACT CCCTCTCTAC TAAAAATACA AAAAATTAGC   2159

TGAGCATGGT GGCGGGCGCC TGTAGTCCCA GCTACTTGGG AGGCTGAGGC AGGAGAATGG   2219

CGTGAACCCA GGAGGCGGAG CTTGCAGTGA GCCGAGATCA CACCACCACA CTCCAGCCTG   2279

GGTGACAGAG CCAGACTCCG TCTCAAAAAA AAAAAAAAAA AAAAAAAAAA AAAAGGGCGG   2339

CCGC                                                                2343
```

(2) INFORMATION FOR SEQ ID NO:2:

(i) SEQUENCE CHARACTERISTICS:
(A) LENGTH: 563 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:2:

```
Met Ala Arg Lys Gln Asn Arg Asn Ser Lys Glu Leu Gly Leu Val Pro
  1               5                  10                  15

Leu Thr Asp Asp Thr Ser His Ala Gly Pro Pro Gly Pro Gly Arg Ala
             20                  25                  30

Leu Leu Glu Cys Asp His Leu Arg Ser Gly Val Pro Gly Gly Arg Arg
         35                  40                  45

Arg Lys Asp Trp Ser Cys Ser Leu Leu Val Ala Ser Leu Ala Gly Ala
     50                  55                  60
```

-continued

```
Phe Gly Ser Ser Phe Leu Tyr Gly Tyr Asn Leu Ser Val Val Asn Ala
 65                  70                  75                  80

Pro Thr Pro Tyr Ile Lys Ala Phe Tyr Asn Glu Ser Trp Glu Arg Arg
                 85                  90                  95

His Gly Arg Pro Ile Asp Pro Asp Thr Leu Thr Leu Leu Trp Ser Val
            100                 105                 110

Thr Val Ser Ile Phe Ala Ile Gly Gly Leu Val Gly Thr Leu Ile Val
        115                 120                 125

Lys Met Ile Gly Lys Val Leu Gly Arg Lys His Thr Leu Leu Ala Asn
    130                 135                 140

Asn Gly Phe Ala Ile Ser Ala Ala Leu Leu Met Ala Cys Ser Leu Gln
145                 150                 155                 160

Ala Gly Ala Phe Glu Met Leu Ile Val Gly Arg Phe Ile Met Gly Ile
                165                 170                 175

Asp Gly Gly Val Ala Leu Ser Val Leu Pro Met Tyr Leu Ser Glu Ile
            180                 185                 190

Ser Pro Lys Glu Ile Arg Gly Ser Leu Gly Gln Val Thr Ala Ile Phe
        195                 200                 205

Ile Cys Ile Gly Val Phe Thr Gly Gln Leu Leu Gly Leu Pro Glu Leu
    210                 215                 220

Leu Gly Lys Glu Ser Thr Trp Pro Tyr Leu Phe Gly Val Ile Val Val
225                 230                 235                 240

Pro Ala Val Val Gln Leu Leu Ser Leu Pro Phe Leu Pro Asp Ser Pro
                245                 250                 255

Arg Tyr Leu Leu Leu Glu Lys His Asn Glu Ala Arg Ala Val Lys Ala
            260                 265                 270

Phe Gln Thr Phe Leu Gly Lys Ala Asp Val Ser Gln Glu Val Glu Glu
        275                 280                 285

Val Leu Ala Glu Ser His Val Gln Arg Ser Ile Arg Leu Val Ser Val
    290                 295                 300

Leu Glu Leu Leu Arg Ala Pro Tyr Val Arg Trp Gln Val Val Thr Val
305                 310                 315                 320

Ile Val Thr Met Ala Cys Tyr Gln Leu Cys Gly Leu Asn Ala Ile Trp
                325                 330                 335

Phe Tyr Thr Asn Ser Ile Phe Gly Lys Ala Gly Ile Pro Pro Ala Lys
            340                 345                 350

Ile Pro Tyr Val Thr Leu Ser Thr Gly Gly Ile Glu Thr Leu Ala Ala
        355                 360                 365

Val Phe Ser Gly Leu Val Ile Glu His Leu Gly Arg Arg Pro Leu Leu
    370                 375                 380

Ile Gly Gly Phe Gly Leu Met Gly Leu Phe Phe Gly Thr Leu Thr Ile
385                 390                 395                 400

Thr Leu Thr Leu Gln Asp His Ala Pro Trp Val Pro Tyr Leu Ser Ile
                405                 410                 415

Val Gly Ile Leu Ala Ile Ile Ala Ser Phe Cys Ser Gly Pro Gly Gly
            420                 425                 430

Ile Pro Phe Ile Leu Thr Gly Glu Phe Phe Gln Gln Ser Gln Arg Pro
        435                 440                 445

Ala Ala Phe Ile Ile Ala Gly Thr Val Asn Trp Leu Ser Asn Phe Ala
    450                 455                 460

Val Gly Leu Leu Phe Pro Phe Ile Gln Lys Ser Leu Asp Thr Tyr Cys
465                 470                 475                 480

Phe Leu Val Phe Ala Thr Ile Cys Ile Thr Gly Ala Ile Tyr Leu Tyr
```

-continued

```
            485                 490                 495

Phe Val Leu Pro Glu Thr Lys Asn Arg Thr Tyr Ala Glu Ile Ser Gln
            500                 505                 510

Ala Phe Ser Lys Arg Asn Lys Ala Tyr Pro Pro Glu Glu Lys Ile Asp
        515                 520                 525

Ser Ala Val Thr Asp Ala Pro Ala Ser Ser Pro Phe Thr Thr Pro Asn
    530                 535                 540

Thr Ala Trp Ile Gln Ala Ala Ala Thr Thr Thr Ala Thr Lys Lys Glu
545                 550                 555                 560

His Pro Leu
```

(2) INFORMATION FOR SEQ ID NO:3:

(i) SEQUENCE CHARACTERISTICS:
(A) LENGTH: 383 amino acids
(B) TYPE: amino acid
(D) TOPOLOGY: linear (ii) MOLECULE TYPE: protein (xi) SEQUENCE DESCRIPTION: SEQ ID NO:3:

```
Met Gly Phe Ser Lys Leu Gly Lys Ser Phe Glu Met Leu Ile Leu Gly
  1               5                  10                  15

Arg Phe Ile Ile Gly Val Tyr Cys Gly Leu Thr Thr Gly Phe Val Pro
            20                  25                  30

Met Tyr Val Gly Glu Val Ser Pro Thr Glu Leu Arg Gly Ala Leu Gly
        35                  40                  45

Thr Leu His Gln Leu Gly Ile Val Val Gly Ile Leu Ile Ala Gln Val
    50                  55                  60

Phe Gly Leu Asp Ser Ile Met Gly Asn Gln Glu Leu Trp Pro Leu Leu
 65                  70                  75                  80

Leu Ser Val Ile Phe Ile Pro Ala Leu Leu Gln Cys Ile Leu Leu Pro
                85                  90                  95

Phe Cys Pro Glu Ser Pro Arg Phe Leu Leu Ile Asn Arg Asn Glu Glu
            100                 105                 110

Asn Arg Ala Lys Ser Val Leu Lys Lys Leu Arg Gly Thr Ala Asp Val
        115                 120                 125

Thr Arg Asp Leu Gln Glu Met Lys Glu Glu Ser Arg Gln Met Met Arg
    130                 135                 140

Glu Lys Lys Val Thr Ile Leu Glu Leu Phe Arg Ser Ala Ala Tyr Arg
145                 150                 155                 160

Gln Pro Ile Leu Ile Ala Val Val Leu Gln Leu Ser Gln Gln Leu Ser
                165                 170                 175

Gly Ile Asn Ala Val Phe Tyr Tyr Ser Thr Ser Ile Phe Glu Lys Ala
            180                 185                 190

Gly Val Gln Gln Pro Val Tyr Ala Thr Ile Gly Ser Gly Ile Val Asn
        195                 200                 205

Thr Ala Phe Thr Val Val Ser Leu Phe Val Val Glu Arg Ala Gly Arg
    210                 215                 220

Arg Thr Leu His Leu Ile Gly Leu Ala Gly Met Ala Gly Cys Ala Val
225                 230                 235                 240

Leu Met Thr Ile Ala Leu Ala Leu Leu Glu Gln Leu Pro Trp Met Ser
                245                 250                 255

Tyr Leu Ser Ile Val Ala Ile Phe Gly Phe Val Ala Phe Phe Glu Val
            260                 265                 270
```

-continued

```
Gly Pro Gly Pro Ile Pro Trp Phe Ile Val Ala Glu Leu Phe Ser Gln
        275                 280                 285

Gly Pro Arg Pro Ala Ala Ile Ala Val Ala Gly Phe Ser Asn Trp Thr
    290                 295                 300

Ser Asn Phe Ile Val Gly Met Cys Phe Gln Tyr Val Glu Gln Leu Cys
305                 310                 315                 320

Gly Pro Tyr Val Phe Ile Ile Phe Thr Val Leu Leu Val Leu Phe Phe
                325                 330                 335

Ile Phe Thr Tyr Phe Lys Val Pro Glu Thr Lys Gly Arg Thr Phe Asp
            340                 345                 350

Glu Ile Ala Ser Gly Phe Arg Gln Gly Gly Ala Ser Gln Ser Asp Lys
        355                 360                 365

Thr Pro Glu Glu Leu Phe His Pro Leu Gly Ala Asp Ser Gln Val
    370                 375                 380
```

(2) INFORMATION FOR SEQ ID NO:4:

(i) SEQUENCE CHARACTERISTICS:
(A) LENGTH: 534 amino acids
(B) TYPE: amino acid
(D) TOPOLOGY: linear (ii) MOLECULE TYPE: protein (xi) SEQUENCE DESCRIPTION: SEQ ID NO:4:

```
Met Asp Gly Lys Ser Lys Met Gln Ala Glu Lys His Leu Thr Gly Thr
  1               5                  10                  15

Leu Val Leu Ser Val Phe Thr Ala Val Leu Gly Phe Phe Gln Tyr Gly
             20                  25                  30

Tyr Ser Leu Gly Val Ile Asn Ala Pro Gln Lys Val Ile Glu Ala His
         35                  40                  45

Tyr Gly Arg Met Leu Gly Ala Ile Pro Met Val Arg His Ala Thr Asn
     50                  55                  60

Thr Ser Arg Asp Asn Ala Thr Ile Thr Val Thr Ile Pro Gly Thr Glu
 65                  70                  75                  80

Ala Trp Gly Ser Ser Glu Gly Thr Leu Ala Pro Ser Ala Gly Phe Glu
                 85                  90                  95

Asp Pro Thr Val Ser Pro His Ile Leu Thr Met Tyr Trp Ser Leu Ser
            100                 105                 110

Val Ser Met Phe Ala Val Gly Gly Met Val Ser Ser Phe Thr Val Gly
        115                 120                 125

Trp Ile Gly Asp Arg Leu Gly Arg Val Lys Ala Met Leu Val Val Asn
    130                 135                 140

Val Leu Ser Ile Ala Gly Asn Leu Leu Met Gly Leu Ala Lys Met Gly
145                 150                 155                 160

Pro Ser His Ile Leu Ile Ile Ala Gly Arg Ala Ile Thr Gly Leu Tyr
                165                 170                 175

Cys Gly Leu Ser Ser Gly Leu Val Pro Met Tyr Val Ser Glu Val Ser
            180                 185                 190

Pro Thr Ala Leu Arg Gly Ala Leu Gly Thr Leu His Gln Leu Ala Ile
        195                 200                 205

Val Thr Gly Ile Leu Ile Ser Gln Val Leu Gly Leu Asp Phe Leu Leu
    210                 215                 220

Gly Asn Asp Glu Leu Trp Pro Leu Leu Leu Gly Leu Ser Gly Val Ala
225                 230                 235                 240

Ala Leu Leu Gln Phe Phe Leu Leu Leu Leu Cys Pro Glu Ser Pro Arg
```

-continued

```
                245                 250                 255

Tyr Leu Tyr Ile Lys Leu Gly Lys Val Glu Glu Ala Lys Lys Ser Leu
            260                 265                 270

Lys Arg Leu Arg Gly Asn Cys Asp Pro Met Lys Glu Ile Ala Glu Met
        275                 280                 285

Glu Lys Glu Lys Gln Glu Ala Ala Ser Glu Lys Arg Val Ser Ile Gly
    290                 295                 300

Gln Leu Phe Ser Ser Ser Lys Tyr Arg Gln Ala Val Ile Val Ala Leu
305                 310                 315                 320

Met Val Gln Ile Ser Gln Gln Phe Ser Gly Ile Asn Ala Ile Phe Tyr
                325                 330                 335

Tyr Ser Thr Asn Ile Phe Gln Arg Ala Gly Val Gly Gln Pro Val Tyr
            340                 345                 350

Tyr Ala Thr Ile Gly Val Gly Val Val Asn Thr Val Phe Thr Val Ile
        355                 360                 365

Ser Val Phe Leu Val Glu Lys Ala Gly Arg Arg Ser Leu Phe Leu Ala
    370                 375                 380

Gly Leu Met Gly Met Leu Ile Ser Ala Val Ala Met Thr Val Gly Leu
385                 390                 395                 400

Val Leu Leu Ser Gln Phe Ala Trp Met Ser Tyr Val Ser Met Val Ala
                405                 410                 415

Ile Phe Leu Phe Val Ile Phe Phe Glu Val Gly Pro Gly Pro Ile Pro
            420                 425                 430

Trp Phe Ile Val Ala Glu Leu Phe Ser Gln Gly Pro Arg Pro Ala Ala
        435                 440                 445

Ile Ala Val Ala Gly Phe Cys Asn Trp Ala Cys Asn Phe Ile Val Gly
    450                 455                 460

Met Cys Phe Gln Tyr Ile Ala Asp Leu Cys Gly Pro Tyr Val Phe Val
465                 470                 475                 480

Val Phe Ala Val Leu Leu Leu Val Phe Phe Leu Phe Ala Tyr Leu Lys
                485                 490                 495

Val Pro Glu Thr Lys Gly Lys Ser Phe Glu Glu Ile Ala Ala Ala Phe
            500                 505                 510

Arg Arg Lys Lys Leu Pro Ala Lys Ser Met Thr Glu Leu Glu Asp Leu
        515                 520                 525

Arg Gly Gly Glu Glu Ala
    530
```

(2) INFORMATION FOR SEQ ID NO:5:

(i) SEQUENCE CHARACTERISTICS:
(A) LENGTH: 494 amino acids
(B) TYPE: amino acid
(D) TOPOLOGY: linear (ii) MOLECULE TYPE: protein (xi) SEQUENCE DESCRIPTION: SEQ ID NO:5:

```
Met Gly Thr Thr Lys Val Thr Thr Pro Leu Ile Phe Ala Ile Ser Ile
  1               5                  10                  15

Ala Thr Ile Gly Ser Phe Gln Phe Gly Tyr Asn Thr Gly Val Ile Asn
             20                  25                  30

Ala Pro Glu Ala Ile Ile Lys Asp Phe Leu Asn Tyr Thr Leu Glu Glu
         35                  40                  45

Arg Ser Glu Thr Pro Pro Ser Ser Val Leu Leu Thr Ser Leu Trp Ser
     50                  55                  60
```

-continued

```
Leu Ser Val Ala Ile Phe Ser Val Gly Gly Met Ile Gly Ser Phe Ser
 65                 70                  75                  80

Val Gly Leu Phe Val Asn Arg Phe Gly Arg Arg Asn Ser Met Leu Ile
                85                  90                  95

Val Asn Leu Leu Ala Ile Ala Gly Gly Cys Leu Met Gly Phe Cys Lys
            100                 105                 110

Ile Ala Glu Ser Val Glu Met Leu Ile Leu Gly Arg Leu Ile Ile Gly
        115                 120                 125

Leu Phe Cys Gly Leu Cys Thr Gly Phe Val Pro Met Tyr Ile Gly Glu
    130                 135                 140

Ile Ser Pro Thr Ala Leu Arg Gly Ala Phe Gly Thr Leu Asn Gln Leu
145                 150                 155                 160

Gly Ile Val Ile Gly Ile Leu Val Ala Gln Ile Phe Gly Leu Lys Val
                165                 170                 175

Ile Leu Gly Thr Glu Asp Leu Trp Pro Leu Leu Leu Gly Phe Thr Ile
            180                 185                 190

Leu Pro Ala Ile Ile Gln Cys Ala Ala Leu Pro Phe Cys Pro Glu Ser
        195                 200                 205

Pro Arg Phe Leu Leu Ile Asn Arg Lys Glu Glu Glu Lys Ala Lys Glu
    210                 215                 220

Ile Leu Gln Arg Leu Trp Gly Thr Glu Asp Val Ala Gln Asp Ile Gln
225                 230                 235                 240

Glu Met Lys Asp Glu Ser Met Arg Met Ser Gln Glu Lys Gln Val Thr
                245                 250                 255

Val Leu Glu Leu Phe Arg Ala Pro Asn Tyr Arg Gln Pro Ile Ile Ile
            260                 265                 270

Ser Ile Met Leu Gln Leu Ser Gln Gln Leu Ser Gly Ile Asn Ala Val
        275                 280                 285

Phe Tyr Tyr Ser Thr Gly Ile Phe Lys Asp Ala Gly Val Gln Glu Pro
    290                 295                 300

Val Tyr Ala Thr Ile Gly Ala Gly Val Val Asn Thr Ile Phe Thr Val
305                 310                 315                 320

Val Ser Val Phe Leu Val Glu Arg Ala Gly Arg Arg Thr Leu His Leu
                325                 330                 335

Ile Gly Leu Gly Gly Met Ala Phe Cys Ser Ile Leu Met Thr Ile Ser
            340                 345                 350

Leu Leu Leu Lys Asp Asn Tyr Ser Trp Met Ser Phe Ile Cys Ile Gly
        355                 360                 365

Ala Ile Leu Val Phe Val Ala Phe Phe Glu Ile Gly Pro Gly Pro Ile
    370                 375                 380

Pro Trp Phe Ile Val Ala Glu Leu Phe Gly Gln Gly Pro Arg Pro Ala
385                 390                 395                 400

Ala Met Ala Val Ala Gly Cys Ser Asn Trp Thr Ser Asn Phe Leu Val
                405                 410                 415

Gly Leu Leu Phe Pro Ser Ala Thr Phe Tyr Leu Gly Ala Tyr Val Phe
            420                 425                 430

Ile Val Phe Thr Val Phe Leu Val Ile Phe Trp Val Phe Thr Phe Phe
        435                 440                 445

Lys Val Pro Glu Thr Arg Gly Arg Thr Phe Glu Glu Ile Thr Arg Ala
    450                 455                 460

Phe Glu Gly Gln Val Gln Thr Gly Thr Arg Gly Glu Lys Gly Pro Ile
465                 470                 475                 480
```

-continued

```
Met Glu Met Asn Ser Ile Gln Pro Thr Lys Asp Thr Asn Ala
                485                 490
```

(2) INFORMATION FOR SEQ ID NO:6:

(i) SEQUENCE CHARACTERISTICS:
(A) LENGTH: 509 amino acids
(B) TYPE: amino acid
(D) TOPOLOGY: linear (ii) MOLECULE TYPE: protein (xi) SEQUENCE DESCRIPTION: SEQ ID NO:6:

```
Met Pro Ser Gly Phe Gln Gln Ile Gly Ser Glu Asp Gly Glu Pro Pro
  1               5                  10                  15

Gln Gln Arg Val Thr Gly Thr Leu Val Leu Ala Val Phe Ser Ala Val
             20                  25                  30

Leu Gly Ser Leu Gln Phe Gly Tyr Asn Ile Gly Val Ile Asn Ala Pro
         35                  40                  45

Gln Lys Val Ile Glu Gln Ser Tyr Asn Glu Thr Trp Leu Gly Arg Gln
     50                  55                  60

Gly Pro Glu Gly Pro Ser Ser Ile Pro Pro Gly Thr Leu Thr Thr Leu
 65                  70                  75                  80

Trp Ala Leu Ser Val Ala Ile Phe Ser Val Gly Gly Met Ile Ser Ser
                 85                  90                  95

Phe Leu Ile Gly Ile Ile Ser Gln Trp Leu Gly Arg Lys Arg Ala Met
            100                 105                 110

Leu Val Asn Asn Val Leu Ala Val Leu Gly Gly Ser Leu Met Gly Leu
        115                 120                 125

Ala Asn Ala Ala Ala Ser Tyr Glu Met Leu Ile Leu Gly Arg Phe Leu
    130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Leu Gly Leu
        195                 200                 205

Thr Val Leu Pro Ala Leu Leu Gln Leu Val Leu Leu Pro Phe Cys Pro
    210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
            260                 265                 270

Leu Ser Leu Leu Gln Leu Leu Gly Ser Arg Thr His Arg Gln Pro Leu
        275                 280                 285

Ile Ile Ala Val Val Leu Gln Leu Ser Gln Gln Leu Ser Gly Ile Asn
    290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Leu Val Glu Arg Ala Gly Arg Arg Thr Leu
```

-continued

```
            340                 345                 350

His Leu Leu Gly Leu Ala Gly Met Cys Gly Cys Ala Ile Leu Met Thr
        355                 360                 365

Val Ala Leu Leu Leu Leu Glu Arg Val Pro Ala Met Ser Tyr Val Ser
    370                 375                 380

Ile Val Ala Ile Phe Gly Phe Val Ala Phe Phe Glu Ile Gly Pro Gly
385                 390                 395                 400

Pro Ile Pro Trp Phe Ile Val Ala Glu Leu Phe Ser Gln Gly Pro Arg
                405                 410                 415

Pro Ala Ala Met Ala Val Ala Gly Phe Ser Asn Trp Thr Ser Asn Phe
            420                 425                 430

Ile Ile Gly Met Gly Phe Gln Tyr Val Ala Glu Ala Met Gly Pro Tyr
        435                 440                 445

Val Phe Leu Leu Phe Ala Val Leu Leu Leu Gly Phe Phe Ile Phe Thr
    450                 455                 460

Phe Leu Arg Val Pro Glu Thr Arg Gly Arg Thr Phe Asp Gln Ile Ser
465                 470                 475                 480

Ala Ala Phe His Arg Thr Pro Ser Leu Leu Glu Gln Glu Val Lys Pro
                485                 490                 495

Ser Thr Glu Leu Glu Tyr Leu Gly Pro Asp Glu Asn Asp
            500                 505
```

(2) INFORMATION FOR SEQ ID NO:7:

(i) SEQUENCE CHARACTERISTICS:
(A) LENGTH: 500 amino acids
(B) TYPE: amino acid
(D) TOPOLOGY: linear (ii) MOLECULE TYPE: protein (xi) SEQUENCE DESCRIPTION: SEQ ID NO:7:

```
Met Glu Gln Gln Asp Gln Ser Met Lys Glu Gly Arg Leu Thr Leu Val
  1               5                  10                  15

Leu Ala Leu Ala Thr Leu Ile Ala Ala Phe Gly Ser Ser Phe Gln Tyr
             20                  25                  30

Gly Tyr Asn Val Ala Ala Val Asn Ser Pro Ala Leu Leu Met Gln Gln
         35                  40                  45

Phe Tyr Asn Glu Thr Tyr Tyr Gly Arg Thr Gly Glu Phe Met Glu Asp
     50                  55                  60

Phe Pro Leu Thr Leu Leu Trp Ser Val Thr Val Ser Met Phe Pro Phe
 65                  70                  75                  80

Gly Gly Phe Ile Gly Ser Leu Leu Val Gly Pro Leu Val Asn Lys Phe
                 85                  90                  95

Gly Arg Lys Gly Ala Leu Leu Phe Asn Asn Ile Phe Ser Ile Val Pro
            100                 105                 110

Ala Ile Leu Met Gly Cys Ser Arg Val Ala Thr Ser Phe Glu Leu Ile
        115                 120                 125

Ile Ile Ser Arg Leu Leu Val Gly Ile Cys Ala Gly Val Ser Ser Asn
    130                 135                 140

Val Val Pro Met Tyr Leu Gly Glu Leu Ala Pro Lys Asn Leu Arg Gly
145                 150                 155                 160

Ala Leu Gly Val Val Pro Gln Leu Phe Ile Thr Val Gly Ile Leu Val
                165                 170                 175

Ala Gln Ile Phe Gly Leu Arg Asn Leu Leu Ala Asn Val Asp Gly Trp
            180                 185                 190
```

-continued

```
Pro Ile Leu Leu Gly Leu Thr Gly Val Pro Ala Ala Leu Gln Leu Leu
        195                 200                 205

Leu Leu Pro Phe Phe Pro Glu Ser Pro Arg Tyr Leu Leu Ile Gln Lys
    210                 215                 220

Lys Asp Glu Ala Ala Ala Lys Lys Ala Leu Gln Thr Leu Arg Gly Trp
225                 230                 235                 240

Asp Ser Val Asp Arg Glu Val Ala Glu Ile Arg Gln Glu Asp Glu Ala
                245                 250                 255

Glu Lys Ala Ala Gly Phe Ile Ser Val Leu Lys Leu Phe Arg Met Arg
            260                 265                 270

Ser Leu Arg Trp Gln Leu Leu Ser Ile Ile Val Leu Met Gly Gly Gln
        275                 280                 285

Gln Leu Ser Gly Val Asn Ala Ile Tyr Tyr Tyr Ala Asp Gln Ile Tyr
    290                 295                 300

Leu Ser Ala Gly Val Pro Glu Glu His Val Gln Tyr Val Thr Ala Gly
305                 310                 315                 320

Thr Gly Ala Val Asn Val Val Met Thr Phe Cys Ala Val Phe Val Val
                325                 330                 335

Glu Leu Leu Gly Arg Arg Leu Leu Leu Leu Leu Gly Phe Ser Ile Cys
            340                 345                 350

Leu Ile Ala Cys Cys Val Leu Thr Ala Ala Leu Ala Leu Gln Asp Thr
        355                 360                 365

Val Ser Trp Met Pro Tyr Ile Ser Ile Val Cys Val Ile Ser Tyr Val
    370                 375                 380

Ile Gly His Ala Leu Gly Pro Ser Pro Ile Pro Ala Leu Leu Ile Thr
385                 390                 395                 400

Ile Phe Leu Gln Ser Ser Arg Pro Ser Ala Phe Met Val Gly Gly Ser
                405                 410                 415

Val His Trp Leu Ser Asn Phe Thr Val Gly Leu Ile Phe Pro Phe Ile
            420                 425                 430

Gln Glu Gly Leu Gly Pro Tyr Ser Phe Ile Val Phe Ala Val Ile Cys
        435                 440                 445

Leu Ile Thr Thr Ile Tyr Ile Phe Leu Ile Val Pro Glu Thr Lys Ala
    450                 455                 460

Lys Thr Phe Ile Glu Ile Asn Gln Ile Phe Thr Lys Met Asn Lys Val
465                 470                 475                 480

Ser Glu Val Tyr Pro Glu Lys Glu Glu Leu Lys Glu Leu Pro Pro Val
                485                 490                 495

Thr Ser Glu Gln
            500
```

(2) INFORMATION FOR SEQ ID NO:8:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: primer (xi) SEQUENCE DESCRIPTION: SEQ ID NO:8:

```
TGTTTCCTAG TCTTTGCTAC A                                            21
```

(2) INFORMATION FOR SEQ ID NO:9:

-continued (i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: primer (xi) SEQUENCE DESCRIPTION: SEQ ID NO:9:

TTGTTAAGGC CTTCCATT 18

(2) INFORMATION FOR SEQ ID NO:10:

(i) SEQUENCE CHARACTERISTICS:
(A) LENGTH: 493 amino acids
(B) TYPE: amino acid
(D) TOPOLOGY: linear (ii) MOLECULE TYPE: protein (xi) SEQUENCE DESCRIPTION: SEQ ID NO:10:

```
Met Xaa Xaa Gly Phe Gln Xaa Gly Ser Val Thr Gly Thr Leu Val Leu
  1               5                  10                  15

Ala Val Leu Ile Ala Ala Leu Gly Ser Phe Gln Tyr Gly Tyr Asn Leu
             20                  25                  30

Gly Val Ile Asn Ala Pro Gln Lys Val Ile Glu Ala Phe Tyr Glu Thr
         35                  40                  45

Trp Leu Gly Arg Xaa Gly Glu Xaa Pro Ser Val Pro Thr Leu Thr Leu
     50                  55                  60

Leu Trp Ser Leu Ser Val Ser Ile Phe Ala Val Gly Gly Met Ile Gly
 65                  70                  75                  80

Ser Phe Leu Val Gly Xaa Ile Gly Asn Arg Leu Gly Arg Lys Xaa Ala
                 85                  90                  95

Met Leu Val Asn Asn Val Leu Ala Ile Ala Gly Gly Leu Leu Met Gly
            100                 105                 110

Leu Ala Lys Xaa Ala Xaa Ser Phe Glu Met Leu Ile Leu Gly Arg Phe
        115                 120                 125

Ile Ile Gly Leu Tyr Cys Gly Leu Ser Ser Gly Val Val Pro Met Tyr
    130                 135                 140

Val Gly Glu Ile Ser Pro Thr Ala Leu Arg Gly Ala Leu Gly Thr Leu
145                 150                 155                 160

Asn Gln Leu Gly Ile Val Ile Gly Ile Leu Ile Ala Gln Val Leu Gly
                165                 170                 175

Leu Asp Ser Leu Leu Gly Asn Glu Ser Leu Trp Pro Leu Leu Leu Gly
            180                 185                 190

Leu Thr Gly Val Pro Ala Leu Leu Gln Leu Leu Leu Leu Pro Phe Cys
        195                 200                 205

Pro Glu Ser Pro Arg Tyr Leu Leu Ile Asn Lys Asn Glu Glu Ala Arg
    210                 215                 220

Ala Lys Lys Ala Leu Gln Arg Leu Arg Gly Thr Ala Asp Val Ser Gln
225                 230                 235                 240

Glu Val Ala Glu Met Lys Asp Glu Ser Arg Xaa Met Xaa Ser Glu Lys
                245                 250                 255

Xaa Val Ser Val Leu Glu Leu Phe Arg Ser Arg Xaa Tyr Arg Gln Pro
            260                 265                 270

Val Ile Ile Ala Ile Val Leu Gln Leu Ser Gln Gln Leu Ser Gly Ile
        275                 280                 285

Asn Ala Val Phe Tyr Tyr Ser Thr Ser Ile Phe Glu Lys Ala Gly Val
```

-continued

```
    290                 295                 300

Gly Gln Pro Val Tyr Ala Thr Ile Gly Ala Gly Val Val Asn Thr Val
305                 310                 315                 320

Phe Thr Val Val Ser Val Phe Val Val Glu Arg Ala Gly Arg Arg Thr
                325                 330                 335

Leu His Leu Leu Gly Leu Gly Gly Met Ala Gly Cys Ala Val Leu Met
            340                 345                 350

Thr Ile Ala Leu Ala Leu Leu Asp Gln Val Pro Trp Met Ser Tyr Val
        355                 360                 365

Ser Ile Val Ala Ile Phe Gly Phe Val Ala Phe Phe Glu Val Gly Pro
    370                 375                 380

Gly Pro Ile Pro Trp Phe Ile Val Ala Glu Leu Phe Ser Gln Gly Pro
385                 390                 395                 400

Arg Pro Ala Ala Ile Ala Val Ala Gly Phe Ser Asn Trp Thr Ser Asn
                405                 410                 415

Phe Ile Val Gly Leu Leu Phe Gln Tyr Ile Ala Glu Leu Leu Gly Pro
            420                 425                 430

Tyr Val Phe Ile Val Phe Ala Val Leu Leu Leu Leu Phe Phe Ile Phe
        435                 440                 445

Thr Phe Leu Lys Val Pro Glu Thr Lys Gly Arg Thr Phe Asp Glu Ile
    450                 455                 460

Ala Ala Ala Phe Arg Lys Xaa Asn Lys Xaa Glu Gln Pro Glu Lys Glu
465                 470                 475                 480

Ser Ile Glu Glu Leu Glu Pro Leu Gly Pro Asp Glu Xaa
                485                 490
```

NUCLEIC ACID MOLECULES ENCODING GLUTX AND USES THEREOF

RELATED APPLICATION INFORMATION

This application is a divisional of application Ser. No. 09/031,392, filed Feb. 26, 1998 now U.S. Pat. No. 5,942,398.

BACKGROUND OF THE INVENTION

A number of mammalian glucose (hexose) transporters (GLUTs) have been identified. High affinity GLUTs are found in nearly every tissue. A low affinity GLUT (GLUT-2) is expressed in tissues which are associated with high glucose flux (e.g., intestine, kidney, and liver). It is thought that the level of expression of high affinity GLUTs influences the rate of glucose uptake. It is also thought that the expression of various GLUTs is regulated by glucose and various hormones (Thorens, *Am. J. Physiol.* 270 (Gastrointest. Liver Physiol. 33:G541–G553, 1996). Human GLUT-1 is described by Mucckler et al. (*Science* 229:941, 1985). Human GLUT-2 is described by Fukumoto et al. (*Proc. Nat'l Acad. Sci. USA* 264:776, 1989). Human GLUT-3 is described by Keller et al. (*J. Biol. Chem.* 264:18884, 1989). Human GLUT-4 is described by Fukumoto et al. (*J. Biol. Chem.* 264:7776, 1989). Human GLUT-5 is described by Kayano et al. (Nature 377:151, 1995).

SUMMARY OF THE INVENTION

The invention described herein relates to the discovery and characterization of a cDNA encoding GLUTX, a human glucose transporter protein. The nucleotide sequence of a cDNA encoding GLUTX is shown in FIGS. 1A–1E. The deduced amino acid sequence of GLUTX is shown in FIGS. 2A–2D. GLUTX is predicted to include 12 transmembrane domains. The first transmembrane domain extends from about amino acid 52 (intracellular end) to about amino acid 71 (extracellular end). The second transmembrane domain extends from about amino acid 108 (extracellular end) to about amino acid 128 (intracellular end). The third transmembrane domain extends from about amino acid 141 (intracellular end) to about amino acid 159 (extracellular end). The fourth transmembrane domain extends from about amino acid 166 (extracellular end) to about amino acid 189 (intracellular end). The fifth transmembrane domain extends from about amino acid 204 (intracellular end) to about amino acid 221 (extracellular end). The sixth transmembrane domain extends from about amino acid 233 (extracellular end) to about amino acid 252 (intracellular end). The seventh transmembrane domain extends from about amino acid 317 (intracellular end) to about amino acid 338 (extracellular end). The eighth transmembrane domain extends from about amino acid 355 (extracellular end) to about amino acid 375 (intracellular end). The ninth transmembrane domain extends from about amino acid 383 (intracellular end) to about amino acid 404 (extracellular end). The tenth transmembrane domain extends from about amino acid 413 (extracellular end) to about amino acid 437 (intracellular end). The eleventh transmembrane domain extends from about amino acid 449 (intracellular end) to about amino acid 472 (extracellular end). The twelfth transmembrane domain extends from about amino acid 481 (extracellular end) to about amino acid 499 (intracellular end). GLUTX nucleic acids and polypeptides, as well as molecules which increase or decrease expression or activity of GLUTX, are useful in the diagnosis and treatment of disorders associated with aberrant hexose transport.

GLUTX protein has some sequence similarity to a number of known glucose transporters (FIGS. 3A–3D).

The invention features isolated nucleic acid molecules (i.e., a nucleic acid molecule that is separated from the 5' and 3' coding sequences with which it is immediately contiguous in the naturally occurring genome of an organism, also referred to as a recombinant nucleic acid molecule) that encodes a GLUTX polypeptide. Within the invention are polypeptides having the sequence of SEQ ID NO:2 or encoded by nucleic acid molecules having the sequence shown in SEQ ID NO:1. However, the invention is not limited to nucleic acid molecules and polypeptides that are identical to those SEQ ID Nos. For example, the invention includes nucleic acid molecules which encode splice variants, allelic variants or mutant forms of GLUTX as well as the proteins encoded by such nucleic acid molecules.

Also within the invention are nucleic acid molecules that hybridize under stringent conditions to a nucleic acid molecule having the sequence of SEQ ID NO:1. Such molecules include, for example, nucleic acid molecules encoding allelic variants of GLUTX or mutant forms of GLUTX. As described further below, molecules that are substantially identical to those of SEQ ID Nos. 1 and 2 are also encompassed by the invention.

The term "substantially pure" as used herein in reference to a given compound (e.g., a GLUTX polypeptide) means that the compound is substantially free from other compounds, such as those in cellular material, viral material, or culture medium, with which the compound may have been associated (e.g., in the course of production by recombinant DNA techniques or before purification from a natural biological source). When chemically synthesized, a compound of the invention is substantially pure when it is substantially free from the chemical compounds used in the process of its synthesis. Polypeptides or other compounds of interest are substantially free from other compounds when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably at least 100 nucleotides (e.g., 150, 200, 250, or 300 nucleotides).

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (e.g., the Sequence Analysis Software Package of the Genetics Computer Group, University of Wisconsin Biotechnology Center, 1710 University Avenue, Madison, Wis. 53705 with the default parameters as specified therein.

The BLAST programs, provided as a service by the National Center for Biotechnology Information (http://www.ncbi.nlm.nih.gov), are very useful for making sequence comparisons. The programs are described in detail by Karlin et al., (*Proc. Natl. Acad. Sci. USA* 87:2264–68, 1990 and 90:5873–7, 1993) and Altschul et al., (*Nucl. Acids Res.* 25:3389–3402, 1997) and are available on the internet at: http://www.ncbi.nlm.nih.gov.

The invention also features a host cell that harbors an isolated nucleic acid molecule encoding GLUTX (either alone or in conjunction with a heterologous polypeptide, such as a detectable marker) or a nucleic acid vector that contains a sequence encoding GLUTX (again, with or without a heterologous polypeptide). The vector can be an expression vector, and the expression vector can include a regulatory element. An antibody that specifically binds a GLUTX polypeptide is also within the scope of the present invention and is useful, for example, to detect GLUTX in a biological sample or to alter the activity of GLUTX. For example, GLUTX can be detected in a biological sample by contacting the sample with an antibody that specifically binds GLUTX under conditions that allow the formation of a GLUTX-antibody complex and detecting the complex, if present, as an indication of the presence of GLUTX in the sample. The use of an antibody in a treatment regime, where it can alter the activity of GLUTX, is discussed further below.

An antibody of the invention can be a monoclonal, polyclonal, or engineered antibody that specifically binds GLUTX (as described more fully below). Antibody that "specifically binds" to a particular antigen, for example, a GLUTX polypeptide of the invention, will not substantially recognize or bind to other molecules in a sample, e.g., a biological sample, that includes GLUTX.

Given that an object of the present invention is to alter the expression or activity of GLUTX in vivo, a pharmaceutical composition containing, for example, an isolated nucleic acid molecule encoding GLUTX (or a fragment thereof), a nucleic acid molecule that is antisense to GLUTX (i.e., that has a sequence that is the reverse and complement of a portion of the coding strand of a GLUTX gene), a GLUTX polypeptide, or an antibody, small molecule, or other compound that specifically binds a GLUTX polypeptide is also a feature of the invention.

The discovery and characterization of GLUTX and the polypeptide it encodes makes it possible to determine whether a given disorder is associated with aberrant expression of GLUTX (either at the transcriptional or translational level) or activity of GLUTX. For example, one can diagnose a patient as having a disorder associated with aberrant expression of GLUTX by measuring GLUTX expression in a biological sample obtained from the patient. An increase or decrease in GLUTX expression in the biological sample, compared with GLUTX expression in a control sample (e.g., a sample of the same tissue collected from one or more healthy individuals) indicates that the patient has a disorder associated with aberrant expression of GLUTX. Similarly, one can diagnose a patient as having a disorder associated with aberrant activity of GLUTX by measuring GLUTX activity in a biological sample obtained from the patient. An increase or decrease in GLUTX activity in the biological sample, compared with GLUTX activity in a control sample, indicates that the patient has a disorder associated with aberrant activity of GLUTX. The techniques required to measure gene expresion or polypeptide activity are well known to those of ordinary skill in the art.

In addition to diagnostic methods, such as those described above, the present invention encompasses methods and compositions for typing and evaluating the prognosis of patients suffering from a disorder associated with aberrant activity or expression of GLUTX. The invention also encompasses methods and compositions for selecting an appropriate an treatment for disorders associated with inappropriate expression of GLUTX or inappropriate activity of GLUTX. The invention also includes compositions and methods for assessing the effectiveness of such treatments. For example, the nucleic acid molecules of the invention can be used as probes to classify cells in terms of their level of GLUTX expression and as primers for diagnostic PCR analysis which can be used to detect mutations, allelic variations, and regulatory defects in the GLUTX gene. Similarly, those of ordinary skill in the art can use routine techniques to identify inappropriate activity of GLUTX, which can be observed in a variety of forms. Diagnostic kits for the practice of such methods are also provided.

The invention further encompasses transgenic animals that express GLUTX and recombinant "knock-out" animals that fail to express GLUTX. These animals can serve as new and useful models of disorders in which GLUTX is misexpressed.

The invention also features antagonists and agonists of GLUTX that can inhibit or enhance, respectively, one or more of the biological activities of GLUTX, e.g., the ability to act as a transporter for certain sugars. Suitable antagonists can include small molecules (i.e., molecules with a molecular weight below about 500), large molecules (i.e., molecules with a molecular weight above about 500), antibodies that specifically bind and "neutralize" GLUTX (as described below), and nucleic acid molecules that interfere with transcription or translation of GLUTX (e.g., antisense nucleic acid molecules and ribozymes). Agonists of GLUTX also include small and large molecules, and antibodies other than neutralizing antibodies.

The invention features methods and compositions useful for identifying antagonists and agonists of a GLUTX biological activity. These methods entail measuring the activity of GLUTX in the presence and absence of a test compound.

The invention also features molecules that can increase or decrease the expression of GLUTX (e.g., by altering transcription or translation). Small molecules (as defined above), large molecules (as defined above), and nucleic acid molecules (e.g., antisense and ribozyme molecules) can be used to inhibit the expression of GLUTX. Other types of nucleic acid molecules (e.g., molecules that bind to GLUTX negative transcriptional regulatory sequences) can be used to increase the expression of GLUTX.

Compounds that modulate the expression of GLUTX in a cell can be identified by comparing the level of expression of GLUTX in the presence of a selected compound with the level of expression of GLUTX in the absence of that compound. A difference in the level of GLUTX expression indicating that the selected compound modulates the expression of GLUTX in the cell. A comparable test for compounds that modulate the activity of GLUTX can be carried out by comparing the level of GLUTX activity in the presence and absence of the compound. Thus, the in The invention features methods and compositions useful for identifying compounds which modulate GLUTX expression. These methods entail measuring the expression of GLUTX (at the transcriptional or translational level) in the presence and absence of a test compound.

Patients who have a disorder mediated by abnormal GLUTX activity can be treated by administration of a compound that alters the expression of GLUTX or the activity of GLUTX. When the objective is to decrease expression or activity, the compound administered can be a GLUTX antisense oligonucleotide or an antibody, such as a neutralizing antibody, that specifically binds GLUTX, respectively.

The preferred methods and materials are described below in examples which are meant to illustrate, not limit, the invention. Skilled artisans will recognize methods and materials that are similar or equivalent to those described herein, and that can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In addition, the materials, methods, and examples are illustrative only and are not intended to be limiting.

Other features and advantages of the invention will be apparent from the detailed description, and from the claims.

BRIEF DESCRIPTION OF THE DRAWINGS

FIGS. 1A–1E is a depiction nucleotide sequence (SEQ ID NO:1) of human GLUTX.

FIGS. 2A–2D is a depiction of the predicted amino acid sequence (SEQ ID NO:2) of human GLUTX.

FIG. 4 also includes plots of antigenicity index (Jameson-Wolf), surface probability (Emini), and hydrophilicity (Kyte-Doolittle).

DETAILED DESCRIPTION

Figure 3A:
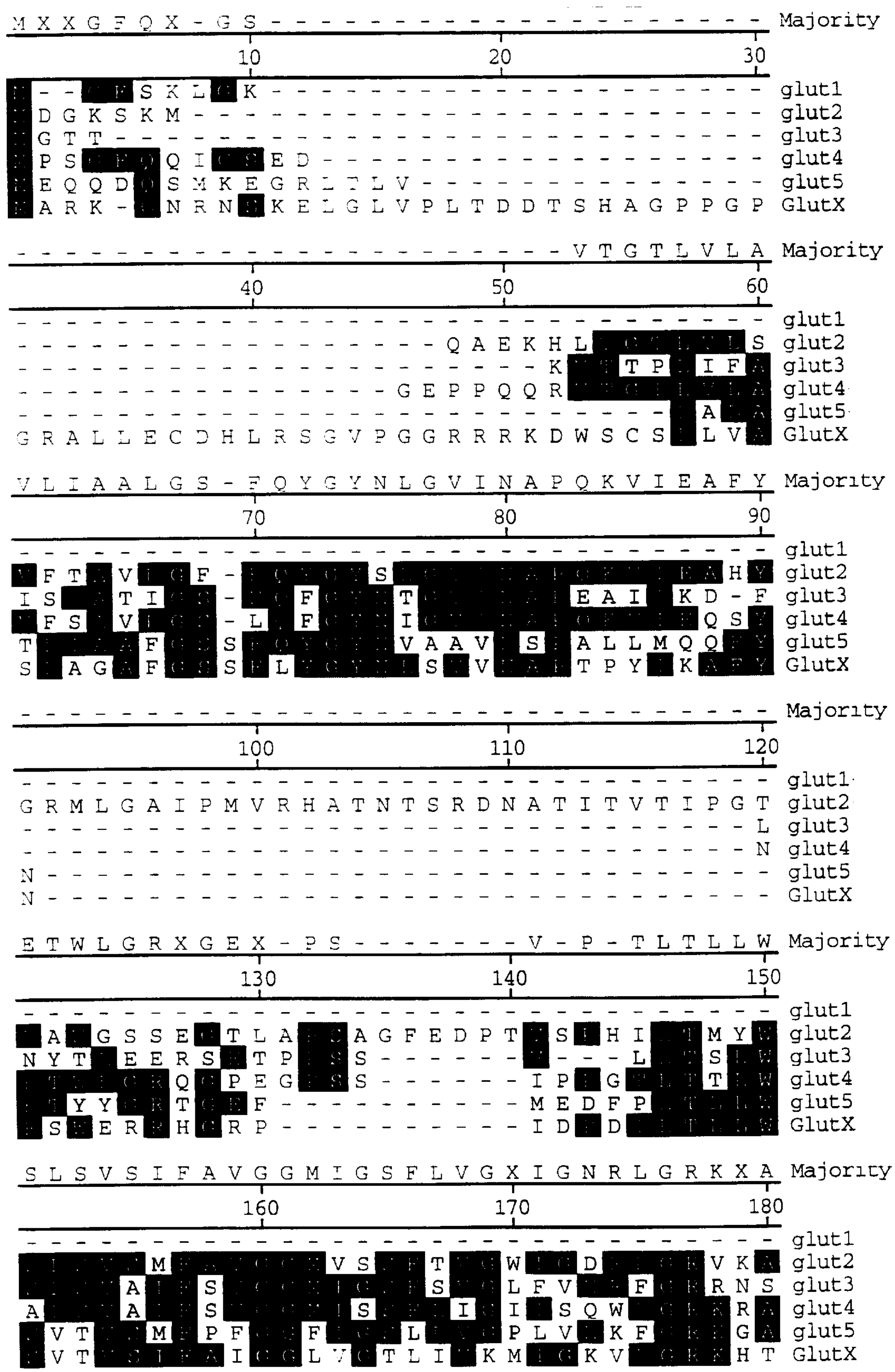
FIGS. 3A–3D is comparison of the amino acid sequences of GLUTX (SEQ ID NO:2), GLUT1 (SEQ ID NO:3), GLUT2 (SEQ ID NO:4), GLUT3 (SEQ ID NO:5), GLUT4 (SEQ ID NO:6), and GLUT5 (SEQ ID NO:7).
Figure 3B:
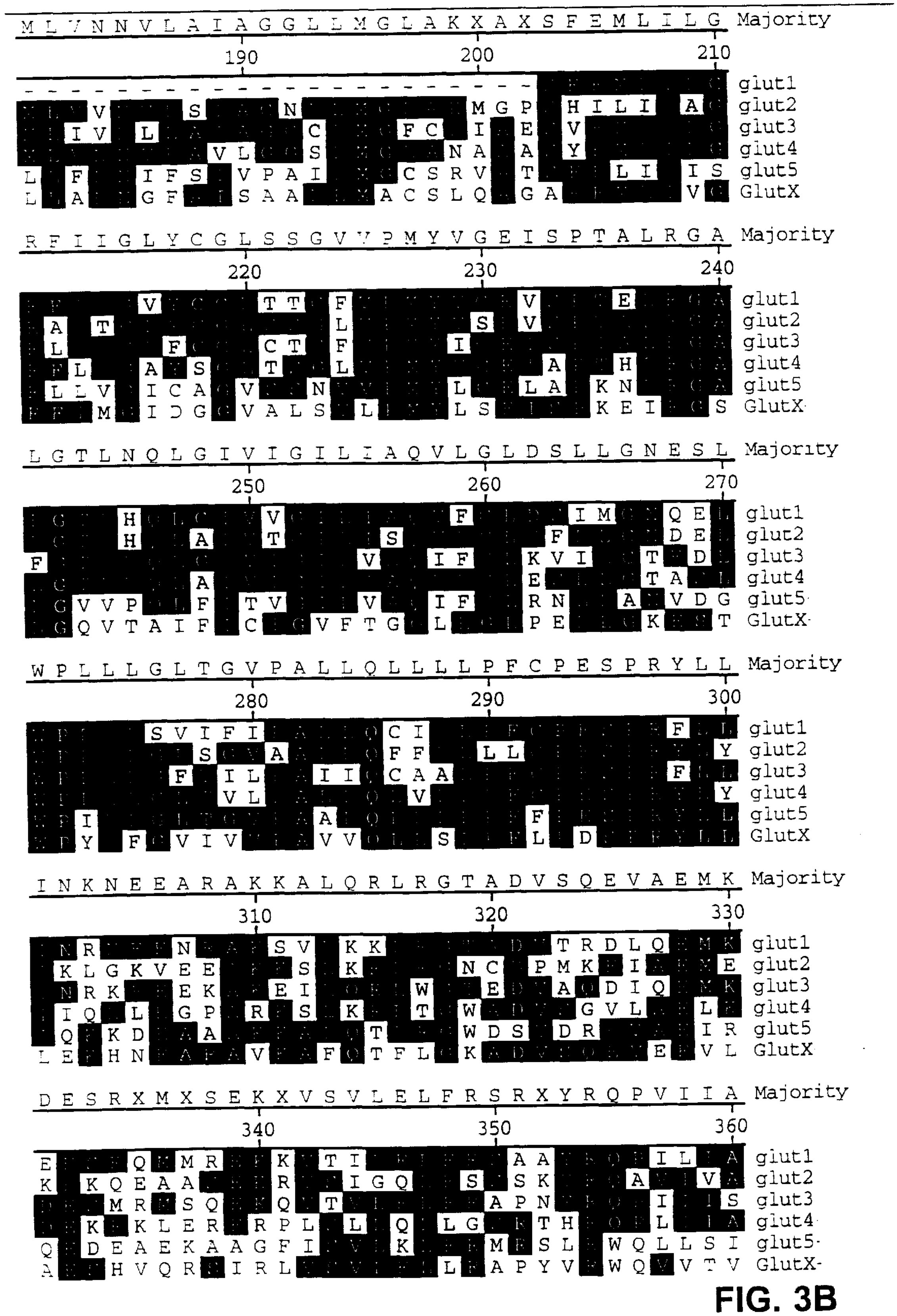
Figure 3C:
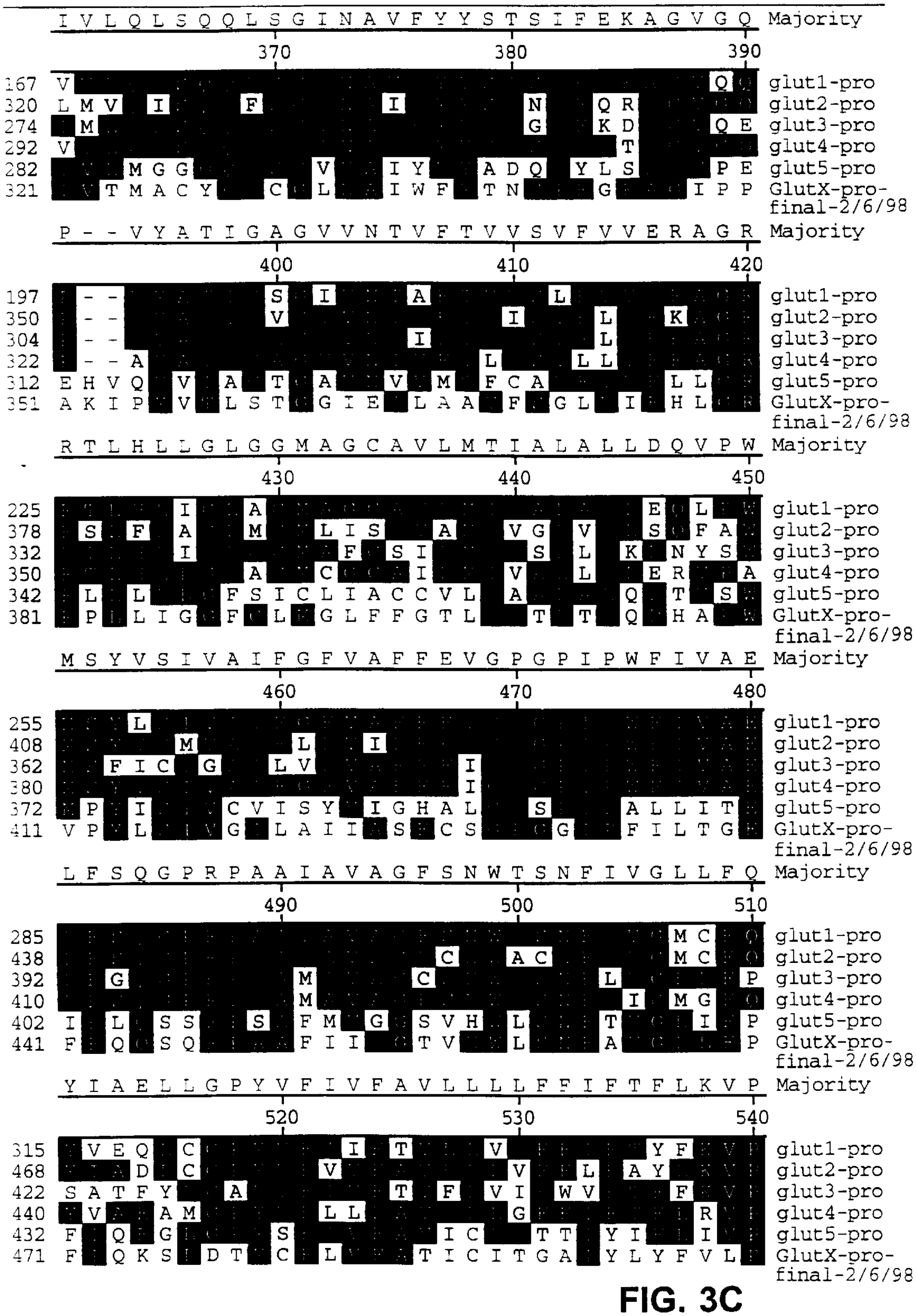
Figure 3D:
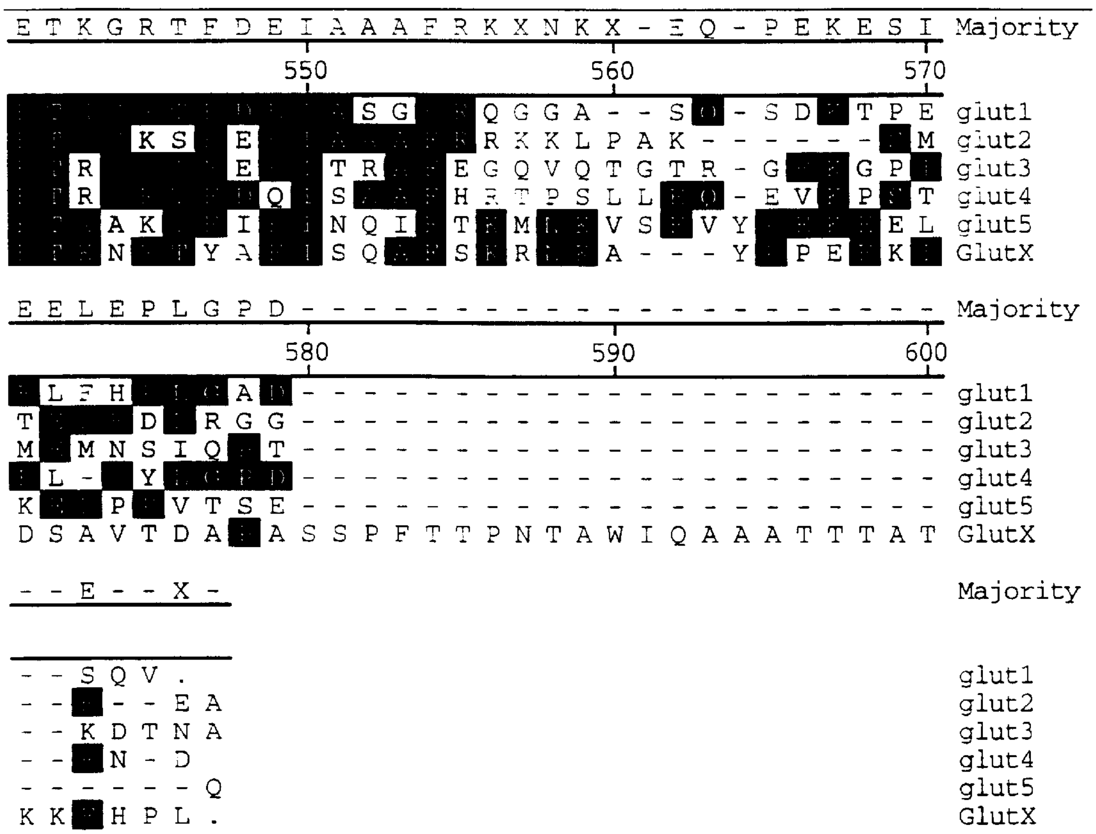

GLUTX is a glucose transporter which has some sequence similarity to members of the GLUT family. GLUTX is predicted to have 12 transmembrane domains. The first transmembrane domain extends from about amino acid 52 (intracellular end) to about amino acid 71 (extracellular end). The second transmembrane domain extends from about amino acid 108 (extracellular end) to about amino acid 128 (intracellular end). The third transmembrane domain extends from about amino acid 141 (intracellular end) to about amino acid 159 (extracellular end). The fourth transmembrane domain extends from about amino acid 166 (extracellular end) to about amino acid 189 (intracellular end). The fifth transmembrane domain extends from about amino acid 204 (intracellular end) to about amino acid 221 (extracellular end). The sixth transmembrane domain extends from about amino acid 233 (extracellular end) to about amino acid 252 (intracellular end). The seventh transmembrane domain extends from about amino acid 317 (intracellular end) to about amino acid 333 (extracellular end). The eighth transmembrane domain extends from about amino acid 355 (extracellular end) to about amino acid 375 (intracellular end). The ninth transmembrane domain extends from about amino acid 383 (intracellular end) to about amino acid 404 (extracellular end). The tenth transmembrane domain extends from about amino acid 413 (extracellular end) to about amino acid 437 (intracellular end). The eleventh transmembrane domain extends from about amino acid 449 (intracellular end) to about amino acid 472 (extracellular end). The twelfth transmembrane domain extends from about amino acid 481 (extracellular end) to about amino acid 499 (intracellular end).

The GLUTX gene was identified as follows. A variety of public and proprietary sequence databases were searched using an approach designed to identify putative glucose transporters. This search led to the identification of an EST which was thought likely to encode a portion of a gene having some similarity to genes encoding previously identified glucose transporters. Two PCR primers (TGTTTCCTAGTCTTTGCTACA; SEQ ID NO:8 and TTGTTAAGGCCTTCCATT; SEQ ID NO:9) based on the sequence of the identified EST were used to screen a human mixed tissue cDNA library. This screening resulted in the identification of a probe which was used to screen the human mixed tissue cDNA library. This screening led to the identification of a number of putative glucose transporter clones. A number of these clones were sequenced and ordered to arrive at a complete sequence for GLUTX. The nucleotide sequence of GLUTX is shown in FIGS. 1A–1E. The predicted amino acid sequence of GLUTX is shown in FIGS. 2A–2D.

The nucleic acid molecules of the invention and the polypeptides they encode (e.g., a GLUTX polypeptide or fragments thereof) can be used directly as diagnostic and therapeutic agents, or they can be used to generate antibodies or identify small molecules that, in turn, are clinically useful. In addition, GLUTX nucleic acid molecules can be used to identify the chromosomal location of GLUTX and as tissue-specific markers. Accordingly, expression vectors containing the nucleic acid molecules of the invention, cells transfected with these vectors, the polypeptides expressed by these cells, and antibodies generated, against either the entire polypeptide or an antigenic fragment thereof, are among the preferred embodiments. These embodiments and some of their clinical application are described further below.

I. Nucleic Acid Molecules Encoding GLUTX

The GLUTX nucleic acid molecules of the invention can be cDNA, genomic DNA, synthetic DNA, or RNA, and can be double-stranded or single-stranded. In the event the nucleic acid molecule is single-stranded, it can be either a sense or an antisense strand. Fragments of these molecules are also considered within the scope of the invention, and can be produced, for example, by the polymerase chain reaction (PCR), or by treating a longer fragment (e.g., a full-length GLUTX gene sequence) with one or more restriction endonucleases. Similarly, a full-length GLUTX mRNA molecule, or a fragment thereof, can be produced by in vitro transcription. The isolated nucleic acid molecule of the invention can encode a fragment of GLUTX that is not found as such in the natural state. Although nucleic acid molecules encoding any given fragment of GLUTX are within the scope of the invention, fragments that retain a biological activity of GLUTX are preferred.

The nucleic acid molecules of the invention encompass recombinant molecules, such as those in which a nucleic acid molecule (e.g., an isolated nucleic acid molecule encoding GLUTX, or a fragment thereof) is incorporated: (1) into a vector (e.g., a plasmid or viral vector), (2) into the genome of a heterologous cell, or (3) into the genome of a homologous cell, at a position other than the natural chromosomal location. Recombinant nucleic acid molecules, transgenic animals, and uses therefor are discussed further below.

The nucleic acid molecules of the invention can contain naturally occurring sequences, or sequences that differ from those that occur naturally, but, due to the degeneracy of the genetic code, encode the same polypeptide. In addition, the nucleic acid molecules of the invention are not limited to those that encode the amino acid residues of the GLUTX polypeptide encoded by SEQ ID NO: 2; they can also include some or all of the non-coding sequences that lie upstream or downstream from a GLUTX coding sequence, a heterologous regulatory element, or a sequence encoding a heterologous polypeptide (e.g., a reporter gene). Regulatory elements and reporter genes are discussed further below.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, goat, horse, pig, rabbit, monkey, dog, or cat. Combinations or modifications of the nucleotides within these types of nucleic acid molecules are also encompassed.

In the event the nucleic acid molecules of the invention encode or act as antisense molecules, they can be used, for example, to regulate translation of GLUTX mRNA. Techniques associated with detection of nucleic acid sequences or regulation of their expression are well known to persons of ordinary skill in the art, and can be used in the context of the present invention to diagnose or treat disorders associated with aberrant GLUTX expression. However, aberrant expression of GLUTX (or aberrant activity of GLUTX) is not a prerequisite for treatment according to the methods of the invention; the molecules of the invention (including the nucleic acid molecules described here) are expected to be useful in improving the symptoms associated with a variety of medical conditions regardless of whether or not the expression of GLUTX (or the activity of GLUTX) is detectably aberrant. Nucleic acid molecules are discussed further below in the context of their clinical utility.

The invention also encompasses nucleic acid molecules that encode other members of the GLUTX family (e.g., the murine homologue of GLUTX). Such nucleic acid molecules will be readily identified by the ability to hybridize under stringent conditions to a nucleic acid molecule encoding a GLUTX polypeptide (e.g., a nucleic acid molecule having the sequence of SEQ ID NO:1). The cDNA sequence described herein (SEQ ID NO:1) can be used to identify these nucleic acids, which include, for example, nucleic acids that encode homologous polypeptides in other species, splice variants of the GLUTX gene in humans or other mammals, allelic variants of the GLUTX gene in humans or other mammals, and mutant forms of the GLUTX gene in humans or other mammals.

The preferred class of nucleic acid molecules that hybridize to SEQ ID NO:1 are nucleic acid molecules that encode human allelic variants of GLUTX. There are two major classes of such variants: active allelic variants, naturally occurring variants that have the biological activity of GLUTX and non-active allelic variants, naturally occurring allelic variants that lack the biological function of GLUTX. Active allelic variants can be used as an equivalent for a GLUTX protein having the amino acid sequence encoded by SEQ ID NO:1 as described herein whereas nonactive allelic variants can be used in methods of disease diagnosis and as a therapeutic target.

The invention features methods of detecting and isolating such nucleic acid molecules. Using these methods, a sample (e.g., a nucleic acid library, such as a cDNA or genomic library) is contacted (or "screened") with a GLUTX-specific probe (e.g., a fragment of SEQ ID NO:1 that is at least 17 nucleotides long). The probe will selectively hybridize to nucleic acids encoding related polypeptides (or to complementary sequences thereof). The term "selectively hybridize" is used to refer to an event in which a probe binds to nucleic acid molecules encoding GLUTX (or to complementary sequences thereof) to a detectably greater extent than to nucleic acids encoding other polypeptides, particularly other types of transporter molecules (or to complementary sequences thereof). The probe, which can contain at least 17 nucleotides (e.g., 18, 20, 25, 50, 100, 150, or 200 nucleotides) can be produced using any of several standard methods (see, e.g., Ausubel et al., "Current Protocols in Molecular Biology, Vol. I," Green Publishing Associates, Inc., and John Wiley & Sons, Inc., N.Y., 1989). For example, the probe can be generated using PCR amplification methods in which oligonucleotide primers are used to amplify a GLUTX-specific nucleic acid sequence (for example, a nucleic acid encoding one of the transmembrane domains) that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the double helix). Complete complementarity between the hybridizing regions is not required in order for a duplex to form; it is only necessary that the number of paired bases is sufficient to maintain the duplex under the hybridization conditions used.

Typically, hybridization conditions initially used to identify related genes are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (e.g., room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (e.g., the content of purine-like nucleotides versus the content of pyrimidine-like nucleotides) and the type of nucleic acid (e.g., DNA or RNA) affect hybridization. An additional consideration is whether one of the nucleic acids is immobilized (e.g., on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acid molecules are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% $NaHPO_4$, 1 M EDTA, 1% BSA) and washing is carried out at 50° C. in 2×SSC.

Preferably, nucleic acid molecules of the invention that are defined by their ability to hybridize with nucleic acid molecules having the sequence shown in SEQ ID NO:1 under stringent conditions will have additional features in common with GLUTX. For example, the nucleic acid molecules identified by hybridization may have a similar, or identical, expression profile as the GLUTX molecule described herein, or may encode a polypeptide having one or more of the biological activities possessed by GLUTX.

Once detected, the nucleic acid molecules can be isolated by any of a number of standard techniques (see, e.g., Sambrook et al., "Molecular Cloning, A Laboratory Manual," 2 nd Ed. Cold Spring Harbor Laboratory Press, Cold Spring Harbor, N.Y., 1989).

The invention also encompasses: (a) expression vectors that contain any of the foregoing GLUTX-related coding sequences and/or their complements (i.e., "antisense" sequence) and fragments thereof; (b) expression vectors that contain any of the foregoing GLUTX-related sequences operatively associated with a regulatory element (examples of which are given below) that directs the expression of the coding sequences; (c) expression vectors containing, in addition to sequences encoding a GLUTX polypeptide, nucleic acid sequences that are unrelated to nucleic acid sequences encoding GLUTX, such as molecules encoding a reporter or marker; and (d) genetically engineered host cells that contain any of the foregoing expression vectors, and thereby express the nucleic acid molecules of the invention in the host cell. The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors.

Additionally, the GLUTX encoding nucleic acid molecules of the present invention can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, a chimeric or hybrid polypeptide of the invention will include a first portion and a second portion; the first portion being a GLUTX polypeptide or a fragment thereof (preferably a biologically active fragment) and the second portion being, for example, the reporter described above or an immunoglobulin constant region.

The expression systems that can be used for purposes of the invention include, but are not limited to, microorganisms such as bacteria (e.g., *E. coli* and *B. subtilis*) transformed with recombinant bacteriophage DNA, plasmid DNA, or cosmid DNA expression vectors containing the nucleic acid molecules of the invention; yeast (e.g., Saccharomyces and Pichia) transformed with recombinant yeast expression vectors containing the nucleic acid molecules of the invention (preferably containing a nucleic acid sequence encoding all or a portion of GLUTX (such as the sequence of SEQ ID NO:1); insect cell systems infected with recombinant virus expression vectors (e.g., baculovirus) containing a nucleic acid molecule of the invention; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing GLUTX nucleotide sequences; or mammalian cell systems (e.g., COS, CHO, BHK, 293, VERO, HeLa, MDCK, WI38, and NIH 3T3 cells) harboring recombinant expression constructs containing promoters derived from the genome of mammalian cells (e.g., the metallothionein promoter) or from mammalian viruses (e.g., the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, e.g., for the generation of pharmaceutical compositions containing GLUTX polypeptides or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J*. 2:1791, 1983), in which the coding sequence of the insert may be ligated individually into the vector in frame with the lacZ coding region so that a fusion protein is produced; pIN vectors (Inouye and Inouye, *Nucleic Acids Res*. 13:3101–3109, 1985; Van Heeke and Schuster, *J. Biol. Chem*. 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhidrosis virus (AcNPV) can be used as a vector to express foreign genes. The virus grows in *Spodoptera frugiperda* cells. The coding sequence of the insert may be cloned individually into non-essential regions (e.g., the polyhedrin gene) of the virus and placed under control of an AcNPV promoter (e.g., the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., *J. Virol*. 46:584, 1983; and Smith, U.S. Pat. No. 4,215,051).

In mammalian host cells, a number of viral-based expression systems may be utilized. In cases where an adenovirus is used as an expression vector, the nucleic acid molecule of the invention can be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a GLUTX gene product in infected hosts (e.g., see Logan and Shenk, *Proc. Natl. Acad. Sci. USA* 81:3655–3659, 1984). Specific initiation signals may also be required for efficient translation of inserted nucleic acid molecules. These signals include the ATG initiation codon and adjacent sequences. In cases where a complete gene or cDNA, including its own initiation codon and adjacent sequences, is inserted into the appropriate expression vector, no additional translational control signals may be needed. However, in cases where only a portion of the coding sequence is inserted (e.g., the portion encoding the mature form of a GLUTX protein) translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol*. 153:516–544, 1987).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. The mammalian cell types listed above are among those that could serve as suitable host cells.

For long-term, high-yield production of recombinant proteins, stable expression is preferred. For example, cell lines which stably express GLUTX can be engineered. Rather than using expression vectors that contain viral origins of replication, host cells can be transformed with DNA controlled by appropriate expression control elements (e.g., promoter sequences, enhancer sequences, transcription terminators, polyadenylation sites, etc.), and a selectable marker. Following the introduction of the foreign DNA, engineered cells can be allowed to grow for 1–2 days in an enriched media, and then switched to a selective media. The selectable marker in the recombinant plasmid confers resistance to the selection, and allows cells to stably integrate the plasmid into their chromosomes and grow to form foci which, in turn, can be cloned and expanded into cell lines. This method can advantageously be used to engineer cell lines that express GLUTX. Such engineered cell lines may be particularly useful in screening and evaluating compounds that affect the endogenous activity of the gene product (i.e., GLUTX).

A number of selection systems can be used. For example, the herpes simplex virus thymidine kinase (Wigler, et al., *Cell* 11:223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in $tk^-$, $hgprt^-$ or $aprt^-$ cells, respectively. Also, anti-metabolite resistance can be used as the basis of selection for the following genes: dhfr, which confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol*. 150:1, 1981); and hygro, which confers resistance to hygromycin (Santerre et al., *Gene* 30:147, 1984).

Alternatively, any GLUTX-containing fusion proteins can be readily purified utilizing an antibody specific for the fusion protein being expressed. For example, a system described by Janknecht et al. allows for the ready purification of non-denatured fusion proteins expressed in human cell lines (*Proc. Natl. Acad. Sci. USA* 88:8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

As implied by the descriptions above, a host cel is any cell into which (or into an ancestor of which) a nucleic acid encoding a polypeptide of the invention (e.g., a GLUTX polypeptide) has been introduced by means of recombinant DNA techniques.

II. GLUTX Polypeptides

The GLUTX polypeptides described herein are those encoded by any of the nucleic acid molecules described above, and include fragments of GLUTX, mutant forms of GLUTX, active and non-active allelic variants of GLUTX, splice variants of GLUTX, truncated forms of GLUTX, and fusion proteins containing all or a portion of GLUTX. These polypeptides can be prepared for a variety of uses including, but not limited to, the generation of antibodies, as reagents in diagnostic assays, for the identification of other cellular gene products or exogenous compounds that can modulate the activity or expression of GLUTX, and as pharmaceutical reagents useful for the treatment of any disorder in which the associated symptoms are improved by altering the activity of GLUTX.

The terms "protein" and "polypeptide" are used herein to describe any chain of amino acid residues, regardless of length or post-translational modification (e.g., modification by glycosylation or phosphorylation). Thus, the term "GLUTX polypeptide" includes full-length, naturally occurring GLUTX polypeptides (that can be purified from tissues in which they are naturally expressed, according to standard biochemical methods of purification), as well as recombinantly or synthetically produced polypeptides that correspond either to a full-length, naturally-occurring GLUTX polypeptide or to particular domains or portions of such a polypeptide. The term also encompasses mature GLUTX having an added amino-terminal methionine (useful for expression in prokaryotic cells).

Preferred polypeptides are substantially pure GLUTX polypeptides that are at least 50% (e.g., 55%, 60%, or 65%), more preferably at least 70% (e.g., 72%, 75%, or 78%), even more preferably at least 80% (e.g., 80%, 85% or 90%), and most preferably at least 95% (e.g., 97% or even 99%) identical to the sequences encoded by SEQ ID NO:1 (e.g., SEQ ID NO:2). Those of ordinary skill in the art are well able to determine the percent identity between two amino acid sequences. Thus, if a polypeptide is encoded by a nucleic acid that hybridizes under stringent conditions with the GLUTX cDNA sequence disclosed herein and also encodes one or more of the conserved regions present in GLUTX, it will be recognized as a GLUTX polypeptide and thereby considered within the scope of the present invention.

The invention also encompasses polypeptides that are functionally equivalent to GLUTX. These polypeptides are equivalent to GLUTX in that they are capable of carrying out one or more of the functions of GLUTX in a biological system. Polypeptides that are functionally equivalent to GLUTX can have 20%, 40%, 50%, 75%, 80%, or even 90% of one or more of the biological activities of the full-length, mature human form of GLUTX. Such comparisons are generally based on an assay of biological activity in which equal concentrations of the polypeptides are used and compared. The comparison can also be based on the amount of the polypeptide required to reach 50% of the maximal biological activity obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the Summary of the Invention.

Polypeptides that are functionally equivalent to GLUTX can be made using random mutagenesis techniques well known to those of ordinary skill in the art (and the resulting mutant GLUTX polypeptides can be tested for activity). It is more likely, however, that such polypeptides will be generated by site-directed mutagenesis (again using techniques well known to persons of ordinary skill in the art). These polypeptides may have increased functionality or decreased functionality.

To design functionally equivalent polypeptides, it is useful to distinguish between conserved positions and variable positions. This can be done by aligning the amino acid sequences of GLUTX that are obtained from various organisms or by aligning GLUTX with other identified glucose transporters, e.g., GLUT1 (SEQ ID NO:3), GLUT2 (SEQ ID NO:4), GLUT3 (SEQ ID NO:5), GLUT4 (SEQ ID NO:6), and GLUT5 (SEQ ID NO:7), shown in FIGS. 3A–3D). Skilled artisans will recognize that conserved amino acid residues are more likely to be necessary for preservation of function. Thus, it is preferable that conserved residues are not altered. Alignment of GLUTX with other glucose receptors will reveal regions that are more highly conserved. Such regions are preferably not altered.

Mutations within the GLUTX coding sequence can be made to generate variant GLUTX genes that are better suited for expression in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N-X-S or N-X-–), and/or an amino acid deletion at the second position of any one or more of such recognition sequences, will prevent glycosylation at the modified tripeptide sequence (see, e.g., Miyajima et al., *EMBO J.* 5:1193, 1986).

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells. In addition, a GLUTX polypeptide can be fused to GST.

The polypeptides of the invention can be chemically synthesized (e.g., see Creighton, "Proteins: Structures and Molecular Principles," W. H. Freeman & Co., N.Y., 1983), or, perhaps more advantageously, produced by recombinant DNA technology as described herein. For additional guidance, persons of ordinary skill in the art may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis, Gait ("Oligonucleotide Synthesis," IRL Press, Oxford, 1984).

III. Transgenic Animals

GLUTX polypeptides can also be expressed in transgenic animals. Such transgenic animals represent model systems for the study of disorders that are either caused by or exacerbated by misexpression of GLUTX, or disorders that can be treated by altering the expression of GLUTX or the activity of GLUTX (even though the expression or activity is not detectably abnormal). Transgenic animals can also be used for the development of therapeutic agents that modulate the expression of GLUTX or the activity of GLUTX.

Transgenic animals can be farm animals (e.g., pigs, goats, sheep, cows, horses, rabbits, and the like) rodents (such as rats, guinea pigs, and mice), non-human primates (e.g., baboons, monkeys, and chimpanzees), and domestic animals (e.g., dogs and cats). Transgenic mice are especially preferred.

Any technique known in the art can be used to introduce a GLUTX transgene into animals to produce founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983).

The present invention provides for transgenic animals that carry a GLUTX transgene in all of their cells, as well as animals that carry a transgene in some, but not all of their cells. For example, the invention provides for mosaic animals. The C-LUTX transgene can be integrated as a single transgene or in concatamers, for example, head-to-head tandems or head-to-tail tandems. The transgene can also be selectively introduced into, and activated in, a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that a GLUTX transgene be integrated into the chromosomal site of an endogenous GLUTX gene, gene targeting is preferred. Briefly, when such a technique is to be used, vectors containing some nucleotide sequences homologous to an endogenous GLULX gene are designed for the purpose of integrating, via homologous recombination with chromosomal sequences, into and disrupting the function Df the nucleotide sequence of the endogenous gene. The transgene also can be selectively introduced into a particular cell type, thus inactivating the endogenous GLUTX gene in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" having no functional GLUTX gene.

Once transgenic animals have been generated, the expression of the recombinant GLUTX gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of GLUTX gene-expressing tissue can also be evaluated immunocytochemically using antibodies specific for the GLUTX transgene product.

For a review of techniques that can be used to generate and assess transgenic animals, those of ordinary skill in the art can consult Gordon (*Intl. Rev. Cytol.* 115:171–229, 1989), and may obtain additional guidance from, for example: Hogan et al. "Manipulating the Mouse Embryo" (Cold Spring Harbor Press, Cold Spring Harbor, N.Y., 1986); Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science* 244:1281, 1986; Wagner et al., U.S. Pat. No. 5,175,385; and Krimpenfort et al., U.S. Pat, No. 5,175,384.

The transgenic animals of the invention can be used to determine the consequence of altering the expression of GLUTX in the context of various disease states. For example, GLUTX knock out mice can be generated using an established line of mice that serve as a model for a disease in which activity of the missing gene is impaired.

IV. Anti-GLUTX Antibodies

GLUTX polypeptides (or immunogenic fragments or analogs thereof) can be used to raise antibodies useful in the invention; such polypeptides can be produced by recombinant techniques or synthesized (see, for example, "Solid Phase Peptide Synthesis," supra; Ausubel et al., supra). In general, GLUTX polypeptides can be coupled to a carrier protein, such as KLH, as described in Ausubel et al., supra, mixed with an adjuvant, and injected into a host mammal. Antibodies produced in that animal can then be purified by peptide antigen affinity chromatography.

In particular, various host animals can be immunized by injection with a GLUTX polypeptide or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and *Corynebacterium parvum*. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, $F(ab')_2$ fragments, and molecules produced using a Fab expression library.

Monoclonal antibodies, which are homogeneous populations of antibodies to a particular antigen, can be prepared using the GLUTX polypeptides described above and standard hybridoma technology (see, for example, Kohler et al., *Nature* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific GLUTX recognition by Western blot or immunoprecipitation analysis by standard methods, for example, as described in Ausubel et al., supra. Antibodies that specifically recognize and bind to GLUTX are useful in the invention. For example, such antibodies can be used in an immunoassay to monitor the level of GLUTX produced by a mammal (e.g., to determine the amount or subcel'ular location of GLUTX).

Figure 4:
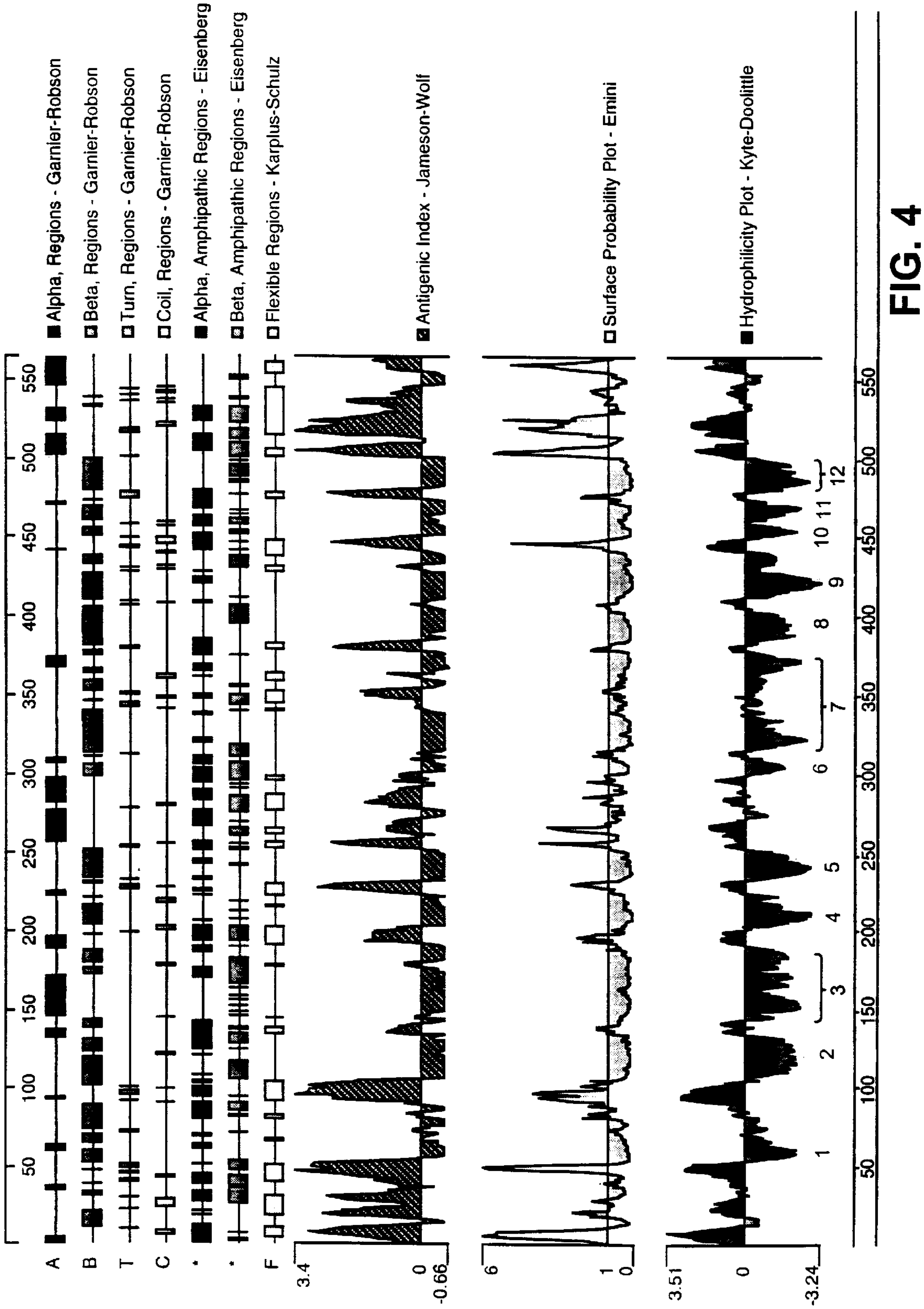
FIG. 4 includes a series of plots predicting various structural features of GLUTX: alpha regions (Garnier-Robson), beta regions (Garnier-Robson), turn regions (Garnier-Robson), coil regions (Garnier-Robson), amphipathic alpha regions (Eisenberg), amphipathic beta regions (Eisenberg), and flexible regions (Karplus-Schult).

Preferably, GLUTX selective antibodies of the invention are produced using fragments of the GLUTX polypeptide that lie outside highly conserved regions and appear likely to be antigenic, by criteria such as high frequency of charged residues. FIG. 4 includes a graph of the antigenicity index (Jameson-Wolf) for GLUTX. This information can be used to design antigenic peptides. Cross-reactive anti-GLUTX antibodies are produced using a fragment of GLUTX that is conserved amongst members of this family of proteins. In one specific example, such fragments are generated by standard techniques of PCR, and are then cloned into the PGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antiserum is also checked for its ability to immunoprecipitate recombinant GLUTX polypeptides or control proteins, such as glucocorticoid receptor, CAT, or luciferase.

The antibodies can be used, for example, in the detection of GLUTX in a biological sample as part of a diagnostic assay or to reduce GLUTX activity as part of a therapeutic regime (e.g., to reduce an undesirable level of GLUTX activity). Antibodies also can be used in a screening assay to measure the effect of a candidate compound on expression or localization of GLUTX. Additionally, such antibodies can be used in conjunction with the gene therapy techniques. For example, they may be used to evaluate the normal and/or engineered GLUTX-expressing cells prior to their introduction into the patient.

In addition, techniques developed for the production of "chimeric antibodies" (Morrison et al., *Proc. Natl. Acad. Sci. USA* 81:6851, 1984; Neuberger et al., *Nature* 312:604, 1984; Takeda et al., *Nature* 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946, 778, and 4,704,692) can be adapted to produce single chain antibodies against a GLUTX polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed (Huse et al., *Science* 246:1275, 1989) to allow rapid and easy identification of monoclonal Fab fragments with the desired specificity.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics* 7:13–21, 1994; see also U.S. Pat. Nos. 5,545,806 and 5,569,825).

The methods described herein, In which anti-GLUTX antibodies are employed, can be performed, for example, by utilizing pre-packaged diagnostic kits comprising at least one specific antibody reagent described herein, which may be conveniently used, for example, in clinical settings, to diagnose patients exhibiting symptoms of the disorders associated with aberrant expression of GLUTX.

V. Antisense Nucleic Acid Molecules

Treatment regimes based on an "antisense" approach involve the design of oligonucleotides (either DNA or RNA) that are complementary to a portion of a selected mRNA. These oligonucleotides bind to complementary mRNA transcripts and prevent their translation. Absolute complementarity, although preferred, is not required. A sequence "complementary" to a portion of an RNA molecule, as referred to herein, is a sequence having sufficient complementarily to hybridize with the RNA, forming a stable duplex; in the case of double-stranded antisense nucleic acids, a single strand of the duplex DNA can be tested, or triplex formation can be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One of ordinary skill in the art can ascertain a tolerable degree of mismatch by use of standard procedures to determine the melting point of the hybridized complex.

Oligonucleotides that are complementary to the 5' end of the message, for example, the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, Nature 372:333, 1984). Thus, oligonucleotides complementary to either the 5' or 3' non-translated, non-coding regions of a GLUTX gene, could be used in an antisense approach to inhibit translation of endogenous GLUTX-mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5', 3', or coding region of GLUTX mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

Regardless of the choice of target sequence, as with other therapeutic strategies directed to GLUTX, it is preferred that in vitro studies are first performed to assess the ability of an antisense oligonucleotide to inhibit gene expression. If desired, the assessment can he quantitative. It is preferred that these studies utilize controls that distinguish between antisense gene inhibition and any nonspecific biological effect that an cligonucleotide may cause. It is also preferred that these studies compare levels of the target RNA or protein with that of an internal control RNA or protein. Additionally, it is envisioned that results obtained using an antisense oligonucleotide are compared with those obtained using a control oligonucleotide. Preferably, the control oligonucleotide is of approximately the same length as the test oligonucleotide, and the nucleotide sequence of the control oligonucleotide differs from that of the test antisense sequence no more than is necessary to prevent specific hybridization between the control oligonucleotide and the targeted RNA sequence.

The oligonucleotides can contain DNA or RNA, or they can contain chimeric mixtures, derivatives, or modified versions thereof that are either single-stranded or double-stranded. The oligonucleotide can be modified at the base moiety, sugar moiety, or phosphate backbone, for example, to improve stability of the molecule, hybridization, etc. Modified sugar moieties can be selected from the group including, but not limited to, arabinose, 2-fluoroarabinose, xylulose, and hexose. A modified phosphate backbone can be selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

The oligonucleotide can include other appended groups such as peptides (e.g., for disrupting the transport properties of the molecule in host cells in vivo), or agents that facilitate transport across the cell membrane (as described, for example, In Letsinger et al., *Proc. Natl. Acad. Sci. USA* 86:6553, 1989; Lemaitre et al., *Proc. Natl. Acad. Sci. USA* 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques* 6:958, 1988), or intercalating agents (see, for example, Zon, *Pharm. Res.* 5:539, 1988). To this end, the oligonucleotide can be conjugated to another molecule, for example, a peptide, a hybridization triggered cross-linking agent, a transport agent, or a hybridization-triggered cleavage agent.

An antisense oligonucleotide of the invention can comprise at least one modified base moiety that is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyamincmethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids. Res.* 15:6625, 1987). The oligonucleotide is a 2'-O-methylribonucleotide (Inoue et al., *Nucl. Acids Res.* 15:6131, 1987), or a chimeric RNA-DNA analog (Inoue et al., *FEBS Lett.* 215:327, 1987).

Antisense oligonucleotides of the invention can be synthesized by standard methods known in the art, for example, by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209, 1988), and methylphosphonate oligonucleotides can be prepared by use of controlled pore glass polymer supports (Sarin et al., *Proc. Natl. Acad. Sci. USA* 85:7448, 1988).

For therapeutic application, antisense molecules of the invention should be delivered to cells that express GLUTX in vivo. A number of methods have been developed for delivering antisense DNA or RNA to cells; for example, antisense molecules can be injected directly into the tissue site. Alternatively, modified antisense molecules, which are designed to target cells that express GLUTX (e.g., antisense molecules linked to peptides or antibodies that specifically bind receptors or antigens expressed on the target cell surface) can be administered systemically.

However, it is often difficult to achieve intracellular concentrations of antisense molecules that are sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with endogenous GLUTX transcripts and thereby prevent translation of GLUTX mRNA. For example, a vector can be introduced in vivo in such a way that it is taken up by a cell and thereafter directs the transcription of an antisense RNA. Such a vector can remain episomal or become chromosomally integrated, as long as it can be transcribed to produce the desired antisense RNA.

Vectors encoding a GLUTX antisense sequence can be constructed by recombinant DNA technology methods that are standard practice in the art. Suitable vectors include plasmid vectors, viral vectors, or other types of vectors known or newly discovered in the art. The criterion for use is only that the vector be capable of replicating and expressing the GLUTX antisense molecule in mammalian cells. Expression of the sequence encoding the antisense RNA can be directed by any promoter known in the art to act in mammalian, and preferably in human, cells. Such promoters can be inducible or constitutively active and include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787–797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988)

VI. Ribozymes

Ribozyme molecules designed to catalytically cleave GLUTX mRNA transcripts also can be used to prevent translation of GLUTX mRNA and expression of GLUTX polypeptides (see, for example, PCT Publication WO 90/11364; Saraver et al., *Science* 247:1222, 1990). While various ribozymes that cleave mRNA at site-specific recognition sequences can be used to destroy GLUTX mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature* 334:585, 1988). There are numerous examples of potential hammerhead ribozyme cleavage sites within the nucleotide sequence of human GLUTX cDNA. Preferably, the ribozyme is engineered so that the cleavage recognition site is located near the 5' end of the GLUTX mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in *Tetrahymena Thermophila* (known as the IVS or L-19 IVS RNA), and which has been extensively described by Cech and his collaborators (Zaug et al., *Science* 224:574, 1984; Zaug et al., *Science* 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in GLUTX.

As in the antisense approach, the ribozymes can be composed of modified oligonucleotides (e.g., for improved stability, targeting, etc.), and should be delivered to cells which express the GLUTX in vivo. A preferred method of delivery involves using a DNA construct "encoding" the ribozyme under the control of a strong constitutive pol III or pol II promoter, so that transfected cells will produce sufficient quantities of the ribozyme to destroy endogenous GLUTX messages and inhibit translation. Because ribozymes, unlike antisense molecules, are catalytic, a lower intracellular concentration is required for efficiency.

VII. Peptide Nucleic Acids

Nucleic acid molecules encoding GLUTX (or a fragment thereof) can be modified at the base moiety, sugar moiety, or phosphate backbone to improve, for example, the stability or solubility of the molecule or its ability to hybridize with other nucleic acid molecules. For example, the deoxyribose phosphate backbone of the nucleic acid can be modified to generate peptide nucleic acids (see Hyrup et al., *Bioorganic Med. Chem.* 4:5–23 (1996). As used herein, the terms "peptide nucleic acids" or "PNAs" refer to nucleic acid mimics, for example, DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., supra; Perry-O'Keefe et al. *Proc. Natl. Acad. Sci. USA* 93:14670–14675 (1996).

PNAs of GLUTX can be used in therapeutic and diagnostic applications. For example, PNAs can be used as antisense or antigene agents for sequence-specific modulation of gene expression by, for example, inducing transcription or translation arrest or inhibiting replication. PNAs of GLUTX can also be used, for example, in the analysis of single base pair mutations in a gene by, for example, PNA-directed PCR clamping; as artificial restriction enzymes when used in combination with other enzymes, for example, S1 nucleases (Hyrup et al., supra); or as probes or primers for DNA sequence and hybridization (Hyrup et al., supra; Perry-O'Keefe, supra).

In other embodiments, PNAs of GLUTX can be modified, for example, to enhance their stability or cellular uptake, by attaching lipophilic or other helper groups to the PNA, by the formation of PNA-DNA chimeras, or by the use of liposomes or other techniques of drug delivery known in the art. For example, PNA-DNA chimeras of GLUTX can be generated that may combine the advantageous properties of PNA and DNA. Such chimeras allow DNA recognition enzymes, for example, RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup et al., supra). The synthesis of PNA-DNA chimeras can be performed as described in Hyrup, supra, and Finn et al., *Nucl. Acids Res.* 24:3357–3363 (1996). For example, a DNA chain can be synthesized on a solid support using standard phosphoramidite coupling chemistry and modified nucleoside analogs, e.g., 5'-(4 methoxytrityl)amino-5'-deoxy-thymidine phosphoramidite, can be used between the PNA and the 5' end of DNA (Mag et al., *Nucl. Acids Res.* 17:5973–5988, 1989). PNA monomers are then coupled in a stepwise manner to produce a chimeric molecule with a 5' PNA segment and a 3' DNA segment (Finn et al., supra). Alternatively, chimeric molecules can be synthesized with a 5' DNA segment and a 3' PNA segment (Peterser et al., *Bioorganic Med. Chem. Lett.* 5:1119–11124 (1975).

In other embodiments, the oligonucleotide may include other appended groups such as peptides (e.g., for targeting host cell receptors in vivo), or agents facilitating transport across the cell membrane (see, e.g., Letsinger et al., *Proc. Natl. Acad. Sci. USA* 86:6553–6556 (1989); Lemaitre et al., *Proc. Natl. Acad. Sci. USA* 84:648652 (1987); PCT Publication No. WO 88/09810, published Dec. 15, 1988) or the blood-brain barrier (see, e.g., PCT Publication No. WO 89/10134, published Apr. 25, 1988). In addition, oligonucleotides can be modified with hybridization-triggered cleavage agents (see, e.g., Krol et al., *BioTech.* 6:958–976 (1988)) or integrating agents (see, e.g., Zon, *Pharm. Res.* 5:539–549 (1988)). To this end, the oligonucleotide may be conjugated to another molecule, for example, a peptide, hybridization triggered cross-linking agent, transport agent, hybridization-triggered cleavage agent etc.

VIII. Proteins that Associate with GLUTX

The invention also features methods for identifying polypeptides that can associate with GLUTX, as well as the isolated interacting protein. Any method that is suitable for detecting protein-protein interactions can be employed to detect polypeptides that associate with GLUTX, whether these polypeptides associate with the transmembrane, intracellular, or extracellular domains of GLUTX. Among the traditional methods that can be employed are co-immunoprecipitation, crosslinking, and co-purification through gradients or chromatographic columns of cell lysates or proteins obtained from cell lysates and the use of GLUTX to identify proteins in the lysate that interact with GLUTX. For these assays, the GLUTX polypeptide can be a full length GLUTX, an extracellular domain of GLUTX, or some other suitable GLUTX polypeptide. Once isolated, such an interacting protein can be identified and cloned and then used, in conjunction with standard techniques, to alter the activity of the GLUTX polypeptide with which it interacts. For example, at least a portion of the amino acid sequence of a protein that interacts with GLUTX can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel, supra; and "PCR Protocols: A Guide to Methods and Applications," Innis et al., eds. Academic Press, Inc., N.Y., 1990).

Additionally, methods can be employed that result directly in the identification of genes that encode proteins that interact with GLUTX. These methods include, for example, screening expression libraries, in a manner similar to the well known technique of antibody probing of λgtll libraries, using labeled GLUTX polypeptide or a GLUTX fusion protein, for example, a GLUTX polypeptide or domain fused to a marker such as an enzyme, fluorescent dye, a luminescent protein, or to an IgFc domain.

There are also methods available that can detect protein-protein interaction in vivo. A method which detects protein interactions in vivo is the two-hybrid system (Chien et al., *Proc. Natl. Acad. Sci. USA* 88:9578, 1991). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding GLUTX, a GLUTX polypeptide, or a GLUTX fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or LacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, GLUTX may be used as the bait gene product. Total genomic or cDNA sequences are fused to the DNA encoding an activation domain. This library and a plasmid encoding a hybrid of bait GLUTX gene product fused to the DNA-binding domain are co-transformed into a yeast reporter strain, and the resulting transformants are screened for those that express the reporter gene. For example, a bait GLUTX gene sequence, such as that encoding GLUTX or a domain of GLUTX can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait GLUTX gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait GLUTX gene-GAL4 fusion plasmid into a yeast strain which contains a lacZ gene driven by a promoter which contains GAL4 activation sequence. A cDNA encoded protein, fused to GAL4 transcriptional activation domain, that interacts with bait GLUTX gene product will reconstitute an active GAL4 protein and thereby drive expression of the HIS3 gene. Colonies that express HIS3 can then be purified from these strains and used to produce and isolate the bait GLUTX gene-interacting protein using techniques routinely practiced in the art.

IX. Detection of GLUTX or Nucleic Acid Molecules Encoding GLUTX and Related Diagnostic Assays The invention encompasses methods for detecting the presence of GLUTX protein or nucleic acid in a biological sample as well as methods for measuring the level of GLUTX protein or nucleic acid in a biological sample. Such methods are useful for diagnosis of disorders associated with aberrant expression of GLUTX.

An exemplary method for detecting the presence or absence of GLUTX in a biological sample involves obtaining a biological sample from a test subject and contacting the biological sample with a compound or an agent capable of detecting a GLUTX polypeptide or a GLUTX nucleic acid (e.g., mRNA or genomic DNA). A preferred agent for detecting GLUTX mRNA or genomic DNA is a labeled nucleic acid probe capable of hybridizing to GLUTX mRNA or genomic DNA. The nucleic acid probe can be, for example, a full-length GLUTX nucleic acid molecule, such as a nucleic acid molecule having the sequence of SEQ ID NO:1, or a portion thereof, such as an oligonucleotide of at least 15, 30, 50, 100, 250, or 500 nucleotides in length and sufficient to specifically hybridize under stringent conditions to GLUTX mRNA or genomic DNA.

A preferred agent for detecting a GLUTX polypeptide is an antibody capable of binding to an GLUTX polypeptide, preferably an antibody with a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells and fluids present within a subject. That is, the detection method of the invention can be used to detect GLUTX mRNA, a GLUTX polypeptide, or GLUTX genomic DNA in a biological sample in vitro as well as in vivo. For example, in vitro techniques for detection of GLUTX mRNA include Northern hybridizations and in situ hybridizations. In vitro techniques for detection of a GLUTX polypeptide include enzyme linked immunosorbent assays (ELISAs), Western blots, immunoprecipitations and immunofluorescence. In vitro techniques for detection of GLUTX genomic DNA include Southern hybridizations. Furthermore, in vivo techniques for detection of a GLUTX polypeptide include introducing into a subject a labeled anti-GLUTX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting a GLUTX polypeptide, GLUTX mRNA, or GLUTX genomic DNA, such that the presence of a GLUTX polypeptide, GLUTX mRNA, or GLUTX genomic DNA is detected in the biological sample, and comparing the presence of GLUTX polypeptide, GLUTX mRNA, or genomic DNA in the control sample with the presence of GLUTX polypeptides, mRNA or genomic DNA in a test sample.

The invention also encompasses kits for detecting the presence of GLUTX nucleic acid molecules or GLUTX polypeptides in a biological sample. For example, the kit can contain a labeled compound or agent capable of detecting a GLUTX polypeptide or a GLUTX mRNA molecule in a biological sample; means for determining the amount of GLUTX in the sample; and means for comparing the amount of GLUTX in the sample with a standard. The compound or agent can be packaged in a suitable container. The kit can further contain instructions for using the kit to detect a GLUTX polypeptide or GLUTX nucleic acid molecule.

X. Prognostic Assays

The invention also encompasses prognostic assays that can be used to identify subjects having or at risk of developing a disease or disorder associated with aberrant GLUTX expression or GLUTX activity. Thus, the present invention provides methods in which a test sample is obtained from a subject and the level, or presence, or allelic form GLUTX nucleic acid molecules or GLUTX polypeptides ia assessed. As used herein, a "test sample" refers to a biological sample obtained from a subject of interest. For example, a test sample can be a biological fluid (e.g., serum), a cell sample, or tissue.

Furthermore, the prognostic assays described herein can be used to determine whether a subject can be administered an agent (e.g., an agonist, antagonist, peptidomimetic, polypeptide, nucleic acid, small molecule or other drug candidate) to treat a disease or disorder associated with aberrant GLUTX expression or GLUTX activity. For example, such methods can be used to determine whether a subject can be effectively treated with an agent that modulates GLUTX expression and/or activity. Thus, the present invention provides methods for determining whether a subject can be effectively treated with an agent for a disorder associated with aberrant GLUTX expression or GLUTX activity in which a test sample is obtained and GLUTX nucleic acids or GLUTX polypeptides are detected (e.g., wherein the presence of a particular level of GLUTX expression or a particular GLUTX allelic variant is diagnostic for a subject that can be administered an agent to treat a disorder associated with aberrant GLUTX expression or GLUTX activity).

The methods of the invention can also be used to detect genetic alterations in a GLUTX. In preferred embodiments, the methods include detecting, in a sample of cells from the subject, the presence or absence of a genetic alteration characterized by at least one alteration affecting the integrity of the gene encoding a GLUTX polypeptide or the misexpression of the GLUTX gene. For example, such genetic alterations can be detected by ascertaining the existence of at least one of: (1) a deletion of one or more nucleotides from a GLUTX gene; (2) an addition of one or more nucleotides to a GLUTX gene; (3) a substitution of one or more nucleotides of a GLUTX gene; (4) a chromosomal rearrangement of a GLUTX gene; (5) an alteration in the level of a messenger RNA transcript of a GLUTX gene; (6) aberrant modification of a GLUTX gene, such as of the methylation pattern of the genomic DNA, (7) the presence of a non-wild type splicing pattern of a messenger RNA transcript of a GLUTX gene; and (10) inappropriate post-translational modification of a GLUTX polypeptide. As described herein, there are a large number of assay techniques known in the art which can be used for detecting alterations in a GLUTX gene.

In certain embodiments, detection of the alteration involves the use of a probe/primer in a polymerase chain reaction (PCR; see, e.g., U.S. Pat. Nos. 4,683,195 and 4,683,202), such as anchor PCR or RACE PCR, or alternatively, in a ligation chain reaction (LCR; see, e.g., Landegran et al., *Science* 241:1077–1080, 1988; and Nakazawa et al. *Proc. Natl. Acad. Sci. USA* 91:360–364, 1994), the latter of which can be particularly useful for detecting point mutations in the GLUTX gene (see Abavaya et al., *Nucl. Acids Res.* 23:675–681, 1995). This method can include the steps of collecting a sample of cells from a patient, isolating nucleic acid (e.g., genomic DNA, mRNA, or both) from the cells of the sample, contacting the nucleic acid sample with one or more primers which specifically hybridize to a GLUTX gene under conditions such that hybridization and amplification of the GLUTX nucleic acid (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., *Proc. Natl. Acad. Sci USA* 87:1874–1878, 1990), transcriptional amplification system (Kwoh et al., *Proc. Natl. Acad. Sci USA* 86:1173–1177, 1989), Q-Beta Replicase (Lizardi et al.,

*Bio/Technology* 6:1197, 1988), or any other nucleic acid amplification method, followed by the detection of the amplified molecules using techniques well known to those of ordinary skill in the art. These detection schemes are especially useful for the detection of nucleic acid molecules if such molecules are present in very low number.

In an alternative embodiment, alterations in a GLUTX gene from a sample cell can be identified by identifying changes in a restriction enzyme cleavage pattern. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498, 531) can be used to score for the presence of specific mutations by development or loss of a ribozyme cleavage site.

In other embodiments, alterations in GLUTX can be identified by hybridizing a sample and control nucleic acids, e.g., DNA or RNA, to high density arrays containing tens to thousands of oligonucleotide probes (Cronin et al., *Human Mutation* 7:244–255, 1996); Kozal et al., *Nature Medicine* 2:753–759, 1996). For example, alterations in GLUTX can be identified in two dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the GLUTX gene and detect mutations by comparing the sequence of the sample GLUTX with the corresponding wild-type (control) sequence. Examples of sequencing reactions include those based on techniques developed by Maxim and Gilbert (*Proc. Natl. Acad. Sci. USA* 74:560 (1977)) or Sanger (*Proc. Natl. Acad. Sci. USA* 74:5463). It is also contemplated that any of a variety of automated sequencing procedures can be utilized when performing the diagnostic assays (*Bio/Techniques* 19:448, 1995) including sequencing by mass spectrometry (see, e.g. PCT International Publication No. WO 94/16101; Cohen et al. *Adv. Chromatogr*. 36:127–162 1996; and Griffin et al., *Appl. Biochem. Biotechnol.* 38:147–159, 1993).

Other methods of detecting mutations in the GLUTX gene include methods in which protection from cleavage agents is used to detect mismatched bases in RNA/RNA or RNA/DNA heteroduplexes (Myers et al. *Science* 230:1242 1985). In general, the art technique of "mismatch cleavage" starts by providing heteroduplexes formed by hybridizing (labeled) RNA or DNA containing the wild-type GLUTX sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with Sl nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. (see, for example, Cotton et al., *Proc. Natl. Acad. Sci. USA* 85:4397 1988; Saleeba et al., *Methods Enzymol.* 217:286–295 1992). In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in GLUTX cDNAs obtained from samples of cells. For example, the mutY enzyme of *E. coli* cleaves A at G/A mismatches (Hsu et al., *Carcinogenesis* 15:1657–1662 1994). According to an exemplary embodiment, a probe based on a GLUTX sequence is hybridized to a cDNA or other DNA product from a test cell or cells. The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility can be used to identify mutations in GLUTX genes. For example, single strand conformation polymorphism (SSCP) can be used to detect differences in electrophoretic mobility between mutant and wild type nucleic acids (Orita et al., *Proc. Natl. Acad. Sci. USA* 86:2766, see also Cotton *Mutat Res.* 285:125–144 1993; and Hayashi *Genet. Anal. Tech. Appl.* 9:73–79 1992). Single-stranded DNA fragments of sample and control GLUTX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the method utilizes heteroduplex analysis to separate double stranded heteroduplex molecules on the basis of changes in electrophoretic mobility (Kee et al., *Trends Genet.* 7:5 1991).

In yet another embodiment, the movement of mutant or wild-type fragments in a polyacrylamide gel containing a gradient of denaturant is assayed using denaturing gradient gel electrophoresis (DGGE; Myers et al., *Nature* 313:495, 1985). When DGGE is used as the method of analysis, DNA will be modified to insure that it does not completely denture, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum et al., *Biophys. Chem.* 265:12753, 1987).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al., *Nature* 324;163, 1986); Saiki et al., *Proc. NAtl. Acad. Sci. USA* 86:6230, 1989). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. oligonucleotides used as primers for specific amplification may carry the mutation of interest in the center of the molecule, so that amplification depends on differential hybridization (Gibbs et al., *Nucl. Acids Res.* 17:2437–2448, 1989) or at the extreme 3' end of one primer where, under appropriate conditions, mismatch can prevent, or reduce polymerase extension (Prossner, *Tib/Tech* 11:238, 1993). In addition it may be desirable to introduce a novel restriction site in the region of the mutation to create cleavage-based detection (Gasparini et al., *Mol. Cell Probes* 6:1, 1992). It is anticipated that in certain embodiments amplification may also be performed using Taq ligase for amplification (Barany, *Proc. Natl. Acad. Sci. USA* 88:89, 1991). In such cases, ligation will occur only if there is a perfect match at the 3' end of the 5' sequence making it possible to detect the presence of a known mutation at a specific site by looking for the presence of absence of amplification.

The methods described herein may be performed, for example, by utilizing pre-packaged diagnostic kits comprising at least one probe nucleic acid or antibody reagent described herein, which may be conveniently used, for example, in a clinical setting to diagnose patient exhibiting symptoms or a family history of a disease or disorder involving abnormal GLUTX activity.

XI. Pharmacogenetics

Agents or modulators which have a stimulatory or inhibitory effect on GLUTX activity (including those that alter activity by altering GLUTX gene expression), identified by a screening assay described herein, can be administered to individuals to treat, prophylactically or therapeutically, disorders associated with aberrant GLUTX activity. In conjunction with such treatment, the pharmacogenetics (i.e., the study of the relationship between an individual's genotype and that individual's response to a foreign compound or drug) of the individual may be considered. Thus, the pharmacogenetics of the individual permits the selection of effective agents (e.g., drugs) for prophylactic or therapeutic treatments based on a consideration of the individual's genotype. Such pharmacogenetics can further be used to determine appropriate dosages and therapeutic regimens. Accordingly, the activity of GLUTX polypeptides, expression of GLUTX nucleic acids, or sequence of GLUTX genes in an individual can be determined and used to thereby select an appropriate agent for therapeutic or prophylactic treatment of the individual.

Pharmacogenetics deals with clinically significant hereditary variations in the response to drugs due to altered drug disposition and abnormal action in affected persons (See, e.g., Eichelbaum, *Clin. Exp. Pharmacol. Physiol.* 23:983–985, 1996 and Linder, *Clin. Chem.* 43:254–266, 1997). In general, two types of pharmacogenetic conditions can be differentiated. Genetic conditions transmitted as single factors altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase (NAT2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the excessive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme is the so called ultra-rapid metabolizers who do not respond to standard doses. Recently, the molecular basis of ultra-rapid metabolism has been identified to be due to CYP2D6 gene amplification.

Thus, the activity of GLUTX polypeptide, expression of GLUTX nucleic acid, or the precise sequence of a GLUTX gene in an individual can be determined and used to select an appropriate agent for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a GLUTX modulator, such as a modulator identified by one of the exemplary screening assays described herein.

XII. Monitoring of Clinical Trials

Monitoring the influence of agents (e.g., drugs, compounds) on the expression of GLUTX or the activity of GLUTX can be applied not only in basic drug screening, but also in clinical trials. For example, the effectiveness of an agent determined by a screening assay as described herein to increase GLUTX gene expression, increase GLUTX polypeptide levels, or upregulate GLUTX activity, can be monitored in clinical trials of subjects exhibiting decreased GLUTX gene expression, decreased GLUTX polypeptide levels, or downregulated GLUTX activity. Alternatively, the effectiveness of an agent determined by a screening assay to decrease GLUTX gene expression, decrease GLUTX polypeptide levels, or downregulate GLUTX activity, can be monitored in clinical trials of subjects exhibiting increased GLUTX gene expression, increased GLUTX polypeptide levels, or upregulated GLUTX activity. In such clinical trials, the expression of GLUTX or activity of GLUTX can be used as a measure of the responsiveness of a particular cell.

For example, and not by way of limitation, genes, including GLUTX, that are modulated in cells by treatment with an agent (e.g., a compound, drug, or small molecule) that modulates GLUTX activity (e.g., identified in a screening assay as described herein) can be identified. Thus, to study the effect of agents on a given disorder, for example, in a clinical trial, the level or expression of GLUTX or other genes implicated in the disorder can be measured. The levels of gene expression (i.e., a gene expression pattern) can be quantified by Northern blot analysis or RT-PCR, as described herein, or alternatively by measuring the amount of polypeptide produced, by one of the methods described herein, or by measuring the levels of activity of GLUTX or other genes. In this way, the gene expression pattern can serve as an indicative marker of the physiological response of the cells to the agent. Accordingly, this response state can be determined before, and at various points during, treatment of the individual with the agent.

In a preferred embodiment, the present invention provides a method for monitoring the effectiveness of treatment of a subject with an agent (e.g., an agonist, antagonist, peptidomimetic, polypeptide, nucleic acid, small molecule, or other drug candidate identified by the screening assays described herein) comprising the steps of (1) obtaining a pre-administration sample from a subject prior to administration of the agent; (2) detecting the level of expression of a GLUTX polypeptide or GLUTX mRNA in the pre-administration sample, or the level or activity of GLUTX; (3) obtaining one or more post-administration samples from the subject; (4) detecting the level of expression of GLUTX polypeptide or GLUTX mRNA or the level or activity of the GLUTX polypeptide in the post-administration sample; (5) comparing the level of expression of GLUTX mRNA in the pre-administration sample with that in the post-administration sample, or comparing the level or activity of the GLUTX polypeptide in the pre-administration sample with that in the post-administration sample; and (6) altering the administration of the agent to the subject accordingly.

XIII. Screening Assays for Compounds that Modulate GLUTX Expression or Activity The invention also encompasses methods for identifying compounds that interact with GLUTX (or a domain of GLUTX) including, but not limited to, compounds that interfere with the interaction of GLUTX with transmembrane, extracellular, or intracellular proteins which regulate GLUTX activity and compounds which modulate GLUTX activity. Also encompasses are method for identifying compounds which bind to GLUTX gene regulatory sequences (e.g., promoter sequences) and which may modulate GLUTX gene expression.

The compounds which may be screened in accordance with the invention include, but are not limited to peptides, antibodies and fragments thereof, and other organic compounds that bind to GLUTX and increase or decrease activity.

Such compounds may include, but are not limited to, peptides such as, for example, soluble peptides, including but not limited to members of random peptide libraries; (Lam et al., *Nature* 354:82–84, 1991; Houghten et al., *Nature* 354:84–86, 1991), and combinatorial chemistry-derived molecular library made of D- and/or L configuration amino acids, phosphopeptides (including, but not limited to, members of random or partially degenerate, directed phosphopeptide libraries; Songyang, et al., *Cell* 72:767–778, 1993), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

Other compounds which can be screened in accordance with the invention include but are not limited to small organic molecules that are able to gain entry into an appropriate cell and affect the expression of the GLUTX gene or activity of GLUTX protein.

Computer modelling and searching technologies permit identification of compounds, or the improvement of already identified compounds, that can modulate GLUTX expression or activity. Having identified such a compound or composition, the active sites or regions are identified. Such active sites might typically be a binding for a natural modulator of activity. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the modulator (or ligand) is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed modulator (ligand), natural or artificial, which may increase the accuracy of the active site structure determined.

If an incomplete or insufficiently accurate structure is determined, the methods of computer-based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential GLUTX modulating compounds.

Alternatively, these methods can be used to identify improved modulating compounds from a previously identified modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Examples of molecular modelling systems are the CHARMm and QUANTA programs (Polygen Corporation; Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen et al., *Acta Pharmaceutical Fennica* 97:159–166, 1993; Ripka, *New Scientist* 54–57 (Jun. 16, 1988); McKinaly and Rossmann, *Annu. Rev. Pharmacol. Toxiciol.* 29:111–122, 1989; Perry and Davies, OSAR: Quantitative Structure-Activity Relationships in Drug Design, pp. 189–193 (Alan R. Liss, Inc. 1989); Lewis and Dean, 1989 Proc. R. Soc. Lond. 236:125–140 and 141–162, 1980; and, with respect to a model receptor for nucleic acid components, Askew et al., *J. Am. Chem. Soc.* 111:1082, 1989. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators of GLUTX activity.

Compounds identified via assays such as those described herein may be useful, for example, in elaborating the biological function of GLUTX and for the treatment of disorders associated with aberrant GLUTX activity or expression. Assays for testing the effectiveness of compounds identified with the above-described techniques are discussed below.

In vitro systems may be designed to identify compounds capable of interacting with GLUTX (or a domain of GLUTX). Compounds identified may be useful, for example, in modulating the activity of wild type and/or mutant GLUTX; may be useful in elaborating the biological function GLUTX; may be utilized in screens for identifying compounds that disrupt normal GLUTX interactions; or may in themselves disrupt such interactions.

The principle of the assays used to identify compounds that bind to GLUTX involves preparing a reaction mixture of GLUTX (or a domain thereof) and the test compound under conditions and for a time sufficient to allow the two components to interact and bind, thus forming a complex which can be removed and/or detected in the reaction mixture. The GLUTX species used can vary depending upon the goal of the screening assay. In some situations it is preferable to employ a peptide corresponding to a domain of GLUTX fused to a heterologous protein or polypeptide that affords advantages in the assay system (e.g., labeling, isolation of the resulting complex, etc.) can be utilized.

The screening assays can be conducted in a variety of ways. For example, one method to conduct such an assay involves anchoring GLUTX protein, polypeptide, peptide or fusion protein or the test substance onto a solid phase and detecting GLUTX/test compound complexes anchored on the solid phase at the end of the reaction. In one embodiment of such a method, the GLUTX reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobillzed component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for GLUTX protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with GLUTX. To this end, cell lines that express GLUTX, or cell lines that have been genetically engineered to express GLUTX can be used.

XIV. Assays for Compounds that Interfere with the Interaction Between GLUTX and a Protein Binding Partner Proteins that interact with the GLUTX are referred to, for purposes of this discussion, as "binding partners". Such binding partners can be involved in regulating GLUTX activity. Therefore, it is desirable to identify compounds that interfere with or disrupt the interaction of such binding partners with GLUTX. Such compounds may be useful in regulating the activity of the GLUTX and treating disorders associated with aberrant GLUTX activity.

The basic principle of the assay systems used to identify compounds that interfere with the interaction between the GLUTX and binding partner or partners involves preparing a reaction mixture containing GLUTX protein, polypeptide, peptide or fusion protein and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the GLUTX moiety and its binding partner. Control reaction mixtures are incubated without the test compound or with a non-active control compound. The formation of any complexes between the GLUTX moiety and the binding partner is then detected. The formation of a complex in the control reaction, but not in the reaction mixture containing the test compound, indicates that the compound interferes with the interaction of GLUTX and the interactive binding partner. Additionally, complex formation within reaction mixtures containing the test compound and normal GLUTX protein may also be compared to complex formation within reaction mixtures containing the test compound and a mutant GLUTX. This comparison may be important in those cases wherein it is desirable to identify compounds that disrupt interactions of mutant but not normal GLUTX.

The assay for compounds that interfere with the interaction of the GLUTX and a binding partner can be conducted in a heterogeneous or homogeneous format. Heterogeneous assays involve anchoring either the GLUTX protein, polypeptide, peptide, or fusion protein, or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the GLUTX moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the GLUTX moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of GLUTX (or a domain thereof) or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface, e.g., using a directly or indirectly labeled antibody specific for the initially non-immobilized species. Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected, e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the GLUTX moiety and the interactive binding partner is prepared in which either the GLUTX or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt GLUTX/intracellular binding partner interaction can be identified.

In a particular embodiment, a GLUTX fusion can be prepared for immobilization. For example, the GLUTX or a peptide fragment thereof can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}I$, for example, by methods routinely practiced in the art. In a heterogeneous assay, the GST-GLUTX fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between GLUTX and the interactive binding partner can be detected by measuring the amount of radioactivity that remains associated with the glutathione-agarose beads. A successful inhibition of the interaction by the test compound will result in a decrease in measured radioactivity.

Alternatively, the GST-GLUTX fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the GLUTX/binding partner interaction can be detected by adding the labeled antibody and measuring the radioactivity associated with the beads.

In another embodiment of the invention, these same techniques can be employed using peptide fragments that correspond to the binding domains of GLUTX and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

XV. Methods for Reducing GLUTX Expression

Expression of GLUTX can be reduced through the use of modulatory compounds identified through the use of the screening methods described above. In addition, endogenous GLUTX gene expression can also be reduced by inactivating or "knocking out" the GLUTX gene or its promoter using targeted homologous recombination (see, for example, U.S. Pat. No. 5,464,764). For example, a mutant, non-functional GLUTX (or a completely unrelated DNA sequence) flanked by DNA homologous to the endogenous GLUTX gene (either the coding regions or regulatory regions of the GLUTX gene) can be used, with or without a selectable marker and/or a negative selectable marker, to transfect cells that express GLUTX-3 in vivo. Insertion of the DNA construct, via targeted homologous recombination, results in inactivation of the GLUTX gene. Such approaches are particularly suited for use in developing animal models to study the role of GLUTX; in this instance, modifications to ES (embryonic stem) cells can be used to generate animal offspring with an inactive GLUTX gene. However, a knock out approach can be adapted for use in humans, provided the recombinant DNA constructs are directly administered or targeted to the required site in vivo using appropriate viral vectors.

Alternatively, endogenous GLUTX gene expression can be reduced by targeting deoxyribonucleotide sequences complementary to the regulatory region of the GLUTX gene (i.e., the GLUTX promoter and/or enhancers) to form triple helical structures that prevent transcription of the GLUTX gene in target cells in the body (Helene, *Anticancer Drug Res.* 6:569, 1981; Helene et al., *Ann. N.Y. Acad. Sci.* 660:27, 1992; and Maher, *Bioassays* 14:807, 1992).

In addition, as discussed above, anti-sense molecules, ribozymes, and peptide nucleic acids can be used to reduce GLUTX expression.

XVI. Assays for the Identification of Compounds that Ameliorate Disorders Associated with Aberrant GLUTX Expression or Activity Compounds, including, but not limited to, compounds identified via assay techniques such as those described above may be useful for the treatment of disorders associated with aberrant GLUTX expression or aberrant GLUTX activity.

While animal model-based assays are particularly useful for the identification of such therapeutic compounds, cell-based assay systems are also very useful, particularly in combination with animal-model based assays. Such cell-based systems can include, for example, recombinant or non-recombinant cells which express GLUTX. The effect of a selected modulatory compound on GLUTX expression can be measured using any of the above-described techniques for measuring GLUTX protein or GLUTX mRNA.

XVII. Effective Dose

Toxicity and therapeutic efficacy of the polypeptides of the invention and the compounds that modulate their expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

XVIII. Formulations and Use

Pharmaceutical compositions for use in accordance with the present invention can be formulated in a conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Alternatively, the active ingredient can be in powder form for constitution with a suitable vehicle, for example, sterile pyrogen-free water, before use.

The compounds can also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (e.g., subcutaneously or intramuscularly) or by intramuscular injection. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The compositions can, if desired, be presented in a pack or dispenser device which may contain one or more unit dosage forms containing the active ingredient. The pack can, for example, comprise metal or plastic foil, such as a blister pack. The pack or dispenser device can be accompanied by instructions for administration.

The therapeutic compositions of the invention can also contain a carrier or excipient, many of which are known to persons of ordinary skill in the art. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol.

The nucleic acids, polypeptides, antibodies, or other modulatory compounds of the invention (i.e., compounds that alter the expression of GLUTX or the activity of GLUTX) can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

XIX. Example

The human GLUTX gene was identified as follows. A variety of public and proprietary sequence databases were searched using an approach designed to identify putative glucose transporters. This search led to the identification of an EST which was thought likely to encode a portion of a gene having some similarity to genes encoding previously identified glucose transporters. Two PCR primers (TGTTTCCTAGTCTTTGCTACA; SEQ ID NO:8 and TTGTTAAGGCCTTCCATT; SEQ ID NO:9) based on the sequence of the identified EST were used to screen a human mixed tissue cDNA library. This screening resulted in the identification of a probe which was used to screen the human mixed tissue cDNA library. This screening led to the identification of a number of putative glucose transporter clones. A number of these clones were sequenced and ordered to arrive at a complete sequence for GLUTX. The nucleotide sequence of GLUTX is shown in FIGS. 1A–1E. The predicted amino acid sequence of GLUTX is also shown in FIGS. 2A–2D.

GLUTX is predicted to have 12 transmembrane domains. The first transmembrane domain extends from about amino acid 52 (intracellular end) to about amino acid 71 (extracellular end). The second transmembrane domain extends from about amino acid 108 (extracellular end) to about amino acid 128 (intracellular end). The third transmembrane domain extends from about amino acid 141 (intracellular end) to about amino acid 159 (extracellular end). The fourth transmembrane domain extends from about amino acid 166 (extracellular end) to about amino acid 189 (intracellular end). The fifth transmembrane domain extends from about amino acid 204 (intracellular end) to about amino acid 221 (extracellular end). The sixth transmembrane domain extends from about amino acid 233 (extracellular end) to about amino acid 252 (intracellular end). The seventh transmembrane domain extends from about amino acid 317 (intracellular end) to about amino acid 333 (extracellular end). The eighth transmembrane domain extends from about amino acid 355 (extracellular end) to about amino acid 375 (intracellular end). The ninth transmembrane domain extends from about amino acid 383 (intracellular end) to about amino acid 404 (extracellular end). The tenth transmembrane domain extends from about amino acid 413 (extracellular end) to about amino acid 437 (intracellular end). The eleventh transmembrane domain extends from about amino acid 449 (intracellular end) to about amino acid 472 (extracellular end). The twelfth transmembrane domain extends from about amino acid 481 (extracellular end) to about amino acid 499 (intracellular end).

FIG. 4 includes a series of plots predicting various structural features of GLUTX: alpha regions (Garnier-Robson), beta regions (Garnier-Robson), turn regions (Garnier-Robson), coil regions (Garnier-Robson), amphipathic alpha regions (Eisenberg), amphipathic beta regions (Eisenberg), and flexible regions (Karplus-Schulz). FIG. 4 also includes plots of antigenicity index (Jameson-Wolf), surface probability (Emini), and hydrophilicity (Kyte-Doolittle).

The predicted amino acid sequence of GLUTX was compared to the amino acid sequences of GLUT1, (SEQ ID NO:3), GLUT2 (SEQ ID NO:4), GLUT3 (SEQ ID NO:5), GLUT4 (SEQ ID NO:6), and GLUT5 (SEQ ID NO:7). This comparison is depicted in FIGS. 3A–3D along with a majority sequence (SEQ ID NO:8). As noted above, in designing variant forms of GLUTX which retain the activity of wild-type GLUTX, it is generally preferable to avoid altering residues that are highly conserved. Of course, if one wished to design a reduced activity variant of GLUTX, it is generally preferable to alter conserved residues. Using sequence comparison information one can design GLUTX variants which are more similar to GLUT1, (SEQ ID NO:3), GLUT2 (SEQ ID NO:4), GLUT3 (SEQ ID NO:5), GLUT4 (SEQ ID NO:6), or GLUT5 (SEQ ID NO:7).

Northern blot analysis carried out using a Clontech Inc. (Palo Alto, Calif.) blot revealed that GLUTX is expressed in the following tissues: liver, kidney, skeletal muscle, and prostate. GLUTX is weakly expressed in the following tissues: small intestine, bladder, placenta, and heart. Finally, this analysis revealed GLUTX expression is not detectable in the following tissues: brain, lung, pancreas, uterus, colon, and stomach.

GLUTX cDNA was inserted into the mammalian expression vector pMET7 (a modified version of pME18S, which utilizes the SRa promoter as described previously; Takebe, *Mol. Cell Bio.* 8:466, 1988) to create a GLUTX expression vector.

The activity of GLUTX and variants thereof may be assessed using any suitable assay. For example, Keller et al. (*J. Biol. Chem.* 264:18884, 1989) describes an assay which can be used to measure the kinetic parameters of hexose transport.

What is claimed is:

1. A substantially pure polypeptide comprising the amino acid sequence of SEQ ID NO:2.

2. A substantially pure polypeptide comprising at least 15 contiguous amino acids of SEQ ID NO:2.

3. The substantially pure polypeptide of claim 2 wherein the polypeptide comprises 25 contiguous amino acids of SEQ ID NO:2.

4. The substantially pure polypeptide of claim 2 wherein the polypeptide comprises 50 contiguous amino acids of SEQ ID NO:2.

5. The substantially pure polypeptide of claim 2 wherein the polypeptide comprises 100 contiguous amino acids of SEQ ID NO:2.

6. The substantially pure polypeptide of any of claims 1–5 wherein the polypeptide is fused to a heterologous polypeptide.

7. A substantially pure polypeptide encoded by a nucleic acid molecule that hybridizes to a nucleic acid molecule consisting of the complement of the nucleotide sequence of SEQ ID NO:1 under conditions of hybridization at 42° C. in 2×SSC/0.1% SDS and washing at 68° C. in 0.1×SSC.

8. A method for detecting in a biological sample the presence of a polypeptide comprising the amino acid sequence of SEQ ID NO:2, the method comprising contacting the biological sample with a compound which selectively binds to a polypeptide consisting of the amino acid sequence of SEQ ID NO:2.

9. A method for detecting in a biological sample the presence of a polypeptide comprising 25 contiguous amino acids of SEQ ID NO:2, the method comprising contacting the biological sample with a compound which selectively binds to a polypeptide consisting of 25 contiguous amino acids of SEQ ID NO:2.

10. A method for detecting in a biological sample the presence of a polypeptide comprising 100 contiguous amino acids of SEQ ID NO:2, the method comprising contacting the biological sample with a compound which selectively binds to a polypeptide consisting of 100 contiguous amino acids of SEQ ID NO:2.

11. The method of any of claims 8–10 wherein the compound is an antibody.

12. A method for identifying a compound which binds to a polypeptide comprising the amino acid sequence of SEQ ID NO:2, the method comprising:

(a) contacting the polypeptide with a test compound; and (b) determining whether the test compound binds to the polypeptide.

13. A method for identifying a compound which binds to a polypeptide comprising 50 contiguous amino acids of SEQ ID NO:2, the method comprising (a) contacting the polypeptide with a test compound; and (b) determining whether the test compound binds to the polypeptide.

14. A method for identifying a compound which binds to a polypeptide comprising the amino acid sequence of SEQ ID NO:2, the method comprising (a) contacting the polypeptide with a test compound; and (b) determining whether the test compound binds to the polypeptide.

* * * * *